(12) United States Patent
Russo et al.

(10) Patent No.: US 10,870,013 B2
(45) Date of Patent: Dec. 22, 2020

(54) MULTI-COIL ELECTROMAGNETIC APPARATUS

(71) Applicant: AAH HOLDINGS LLC, Pinehurst, NC (US)

(72) Inventors: Francis J. Russo, Glen Head, NY (US); André DiMino, Woodcliff Lake, NJ (US)

(73) Assignee: AAH HOLDINGS LLC, Pinehurst, NC (US)

( * ) Notice: Subject to any disclaimer, the term of this patent is extended or adjusted under 35 U.S.C. 154(b) by 207 days.

(21) Appl. No.: 15/972,458

(22) Filed: May 7, 2018

(65) Prior Publication Data

US 2018/0318598 A1 Nov. 8, 2018

Related U.S. Application Data

(60) Provisional application No. 62/503,065, filed on May 8, 2017.

(51) Int. Cl.
| | | |
|---|---|---|
| *A61N 2/02* | (2006.01) | |
| *A61N 2/00* | (2006.01) | |
| *A61B 18/18* | (2006.01) | |
| *G06K 19/07* | (2006.01) | |
| *A61N 1/40* | (2006.01) | |

(52) U.S. Cl.
CPC ............... *A61N 2/02* (2013.01); *A61B 18/18* (2013.01); *A61N 1/40* (2013.01); *A61N 2/002* (2013.01); *G06K 19/0723* (2013.01)

(58) Field of Classification Search
CPC .......... A61N 2/00; A61N 2/004; A61N 2/006; A61N 2/008

USPC ....................................................... 600/9–15
See application file for complete search history.

(56) References Cited

U.S. PATENT DOCUMENTS

| | | |
|---|---|---|
| 4,556,051 A | 12/1985 | Maurer |
| 5,565,005 A | 10/1996 | Erickson et al. |
| 5,584,863 A | 12/1996 | Conyers et al. |
| 5,723,001 A | 3/1998 | Pilla et al. |
| 5,766,231 A | 6/1998 | Erickson et al. |

(Continued)

FOREIGN PATENT DOCUMENTS

| | | |
|---|---|---|
| CN | 101415462 A | 4/2009 |
| CN | 101444074 A | 5/2009 |

(Continued)

OTHER PUBLICATIONS

Pilla et al., "EMF signals and ion/ligand binding kinetics: prediction of bioeffective waveform parameters," Bioelectrochemistry and Bioenergetics, vol. 48, Issue 1, pp. 27-34, Feb. 1999.

*Primary Examiner* — Samuel G Gilbert
(74) *Attorney, Agent, or Firm* — Amster, Rothstein & Ebenstein LLP

(57) ABSTRACT

A pulsed electromagnetic field (PEMF) treatment apparatus having electrically-conductive loops arranged within an enclosure to form an array, each of the electrically-conductive loops having a generally circular circumference with one or more indentations aligned with a corresponding indentation of an adjacent electrically-conductive loop, where PEMF signals are generated through the array of electrically-conductive loops based on proximity detection conducted by a corresponding wireless device.

21 Claims, 18 Drawing Sheets

(56) References Cited

U.S. PATENT DOCUMENTS

| | | |
|---|---|---|
| 7,611,453 B2 | 11/2009 | Pilla et al. |
| 7,740,574 B2 | 6/2010 | Pilla |
| 7,744,524 B2 | 6/2010 | Pilla |
| 7,758,490 B2 | 7/2010 | Pilla |
| 7,783,348 B2 | 8/2010 | Gill et al. |
| 7,896,797 B2 | 3/2011 | Pilla |
| 8,343,027 B1 | 1/2013 | DiMino et al. |
| 8,415,123 B2 | 4/2013 | Pilla |
| 8,768,454 B2 | 7/2014 | Sham et al. |
| 8,961,385 B2 | 2/2015 | Pilla et al. |
| 9,005,101 B1* | 4/2015 | Van Erlach .......... A61B 5/4836 600/9 |
| 9,320,913 B2 | 4/2016 | DiMino et al. |
| 9,387,339 B2 | 7/2016 | Sham et al. |
| 9,415,233 B2 | 8/2016 | Pilla et al. |
| 9,427,598 B2 | 8/2016 | Pilla et al. |
| 9,433,797 B2 | 9/2016 | Pilla et al. |
| 9,440,089 B2 | 9/2016 | Pilla et al. |
| 9,656,096 B2 | 5/2017 | Pilla |
| 9,849,299 B2 | 12/2017 | Sham et al. |
| 9,968,797 B2 | 5/2018 | Sham et al. |
| 2005/0251229 A1 | 11/2005 | Pilla et al. |
| 2006/0212077 A1 | 9/2006 | Pilla et al. |
| 2007/0026514 A1 | 2/2007 | Pilla et al. |
| 2007/0173904 A1 | 7/2007 | Pilla |
| 2007/0300140 A1 | 12/2007 | Makela et al. |
| 2008/0058793 A1 | 3/2008 | Pilla et al. |
| 2008/0125618 A1* | 5/2008 | Anderson ................ A61N 2/02 600/14 |
| 2008/0132971 A1 | 6/2008 | Pilla et al. |
| 2008/0140155 A1 | 6/2008 | Pilla et al. |
| 2010/0210893 A1 | 8/2010 | Pilla |
| 2010/0222631 A1 | 9/2010 | Pilla |
| 2011/0112352 A1 | 5/2011 | Pilla et al. |
| 2012/0089201 A1 | 4/2012 | Pilla et al. |
| 2013/0218235 A9 | 8/2013 | Pilla |
| 2013/0274540 A1 | 10/2013 | Pilla |
| 2014/0046117 A1 | 2/2014 | Pilla et al. |
| 2014/0046232 A1 | 2/2014 | Sham et al. |
| 2014/0213843 A1 | 7/2014 | Pilla et al. |
| 2014/0303425 A1 | 10/2014 | Pilla et al. |
| 2014/0343351 A1* | 11/2014 | Tojo ........................ A61N 2/02 600/14 |
| 2015/0196771 A1 | 7/2015 | Pilla et al. |
| 2015/0217126 A1 | 8/2015 | Pilla |
| 2016/0121135 A1 | 5/2016 | Pilla |
| 2017/0080245 A1 | 3/2017 | DiMino et al. |

FOREIGN PATENT DOCUMENTS

| | | |
|---|---|---|
| CN | 1980610 A | 5/2010 |
| CN | 101432041 B | 4/2012 |
| CN | 104023790 A | 9/2014 |
| WO | 1995/33514 A1 | 12/1995 |
| WO | 200505611 A2 | 6/2005 |
| WO | 2005102188 A1 | 11/2005 |
| WO | 2013067512 A1 | 5/2013 |
| WO | 2018208673 A1 | 11/2018 |

* cited by examiner

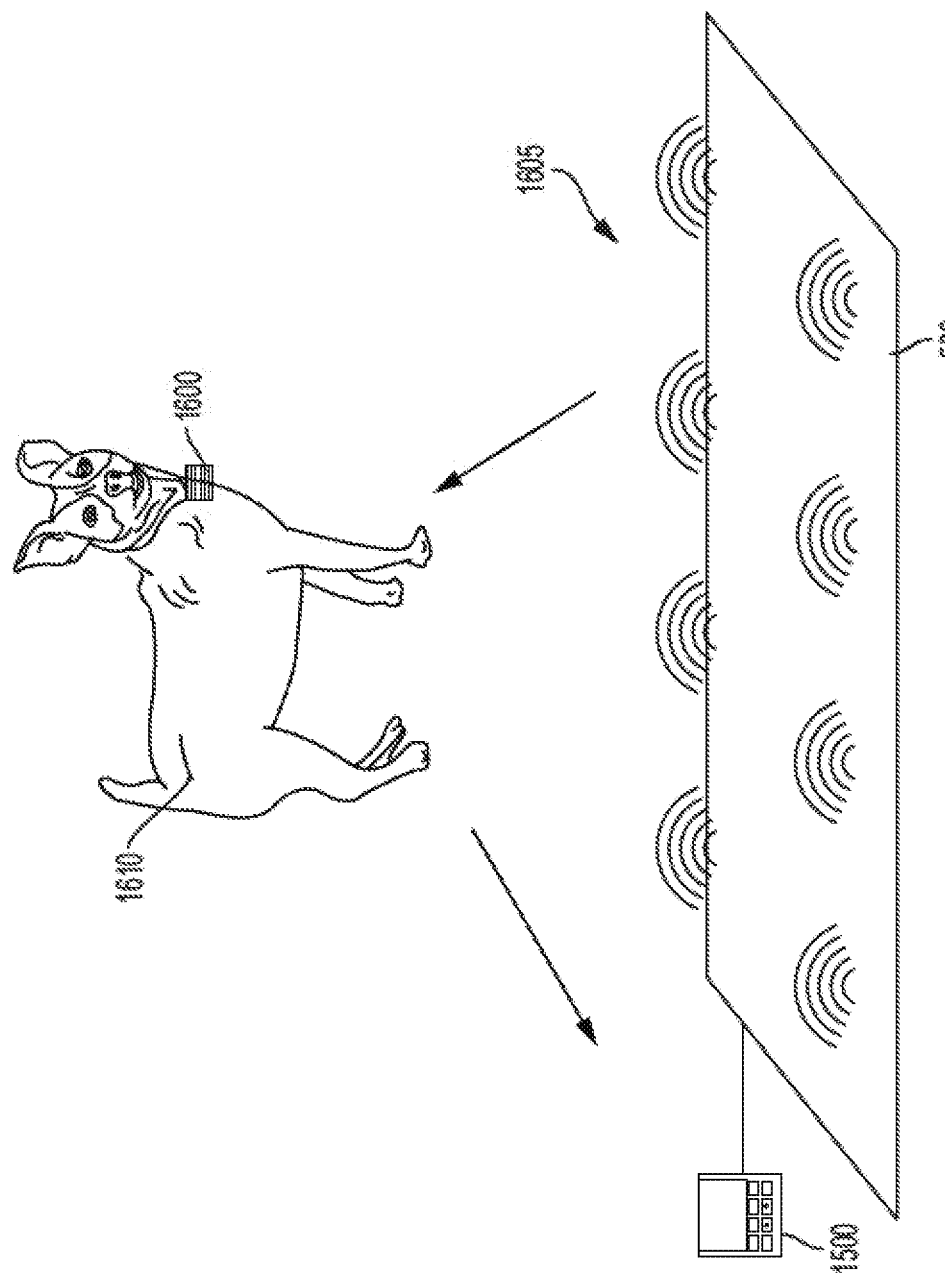

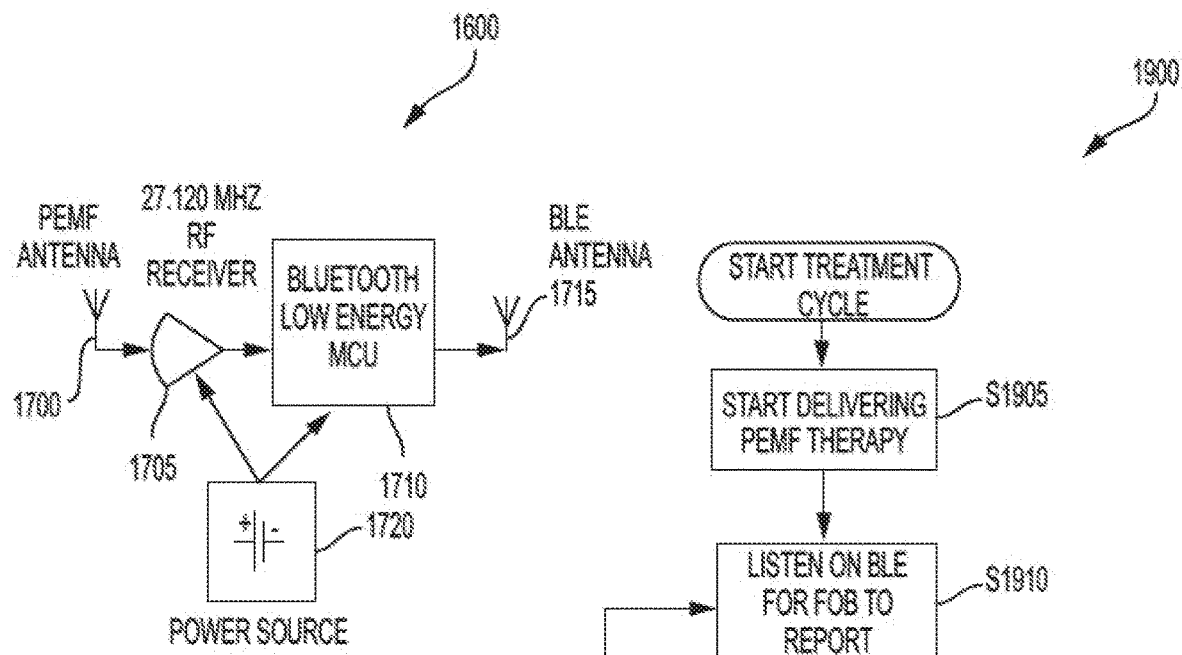
FIG. 5C
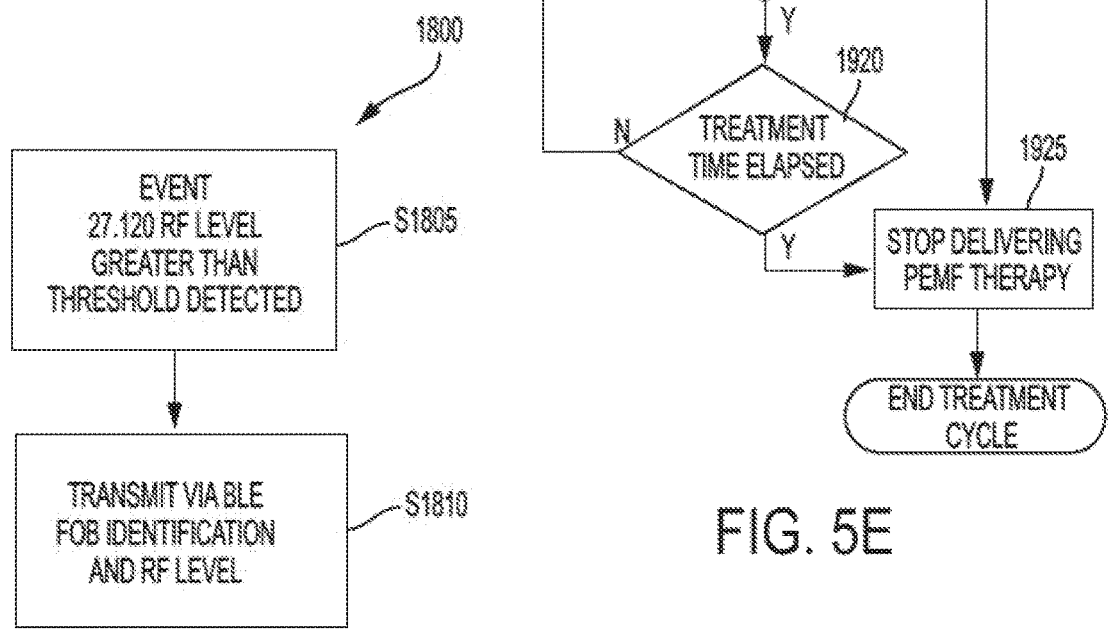
FIG. 5D
FIG. 5E

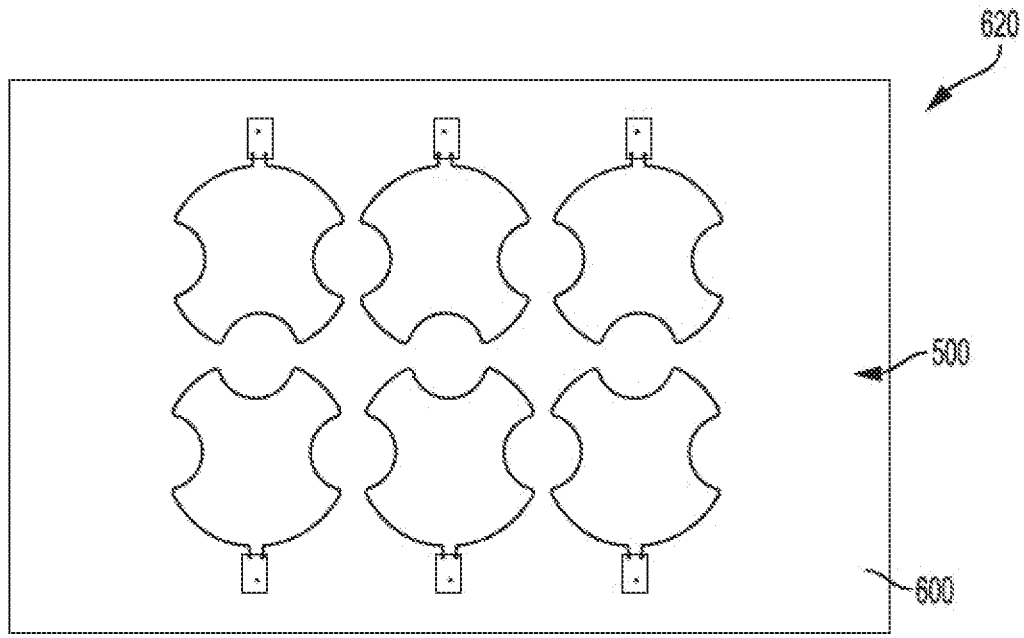
FIG. 6B
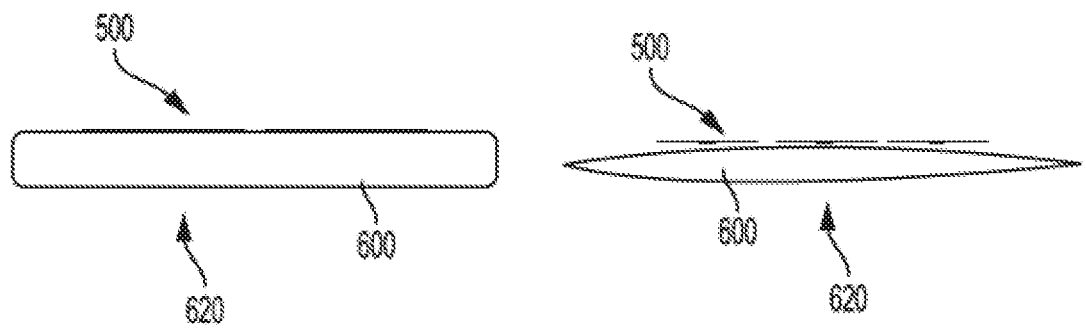
FIG. 6C
FIG. 6D

MULTI-COIL ELECTROMAGNETIC APPARATUS

CROSS-REFERENCE TO RELATED APPLICATION

The present application claims the benefit of and priority to U.S. Provisional Patent Application No. 62/503,065, filed on May 8, 2017, the entire contents of which are incorporated by reference herein.

FIELD OF THE INVENTION

The present invention relates to methods and apparatuses for applying pulsed electromagnetic field (PEMF) signals in non-invasive anti-inflammatory therapy and tissue healing and growth promotion treatments in humans and animals.

BACKGROUND OF THE INVENTION

The application of PEMF signals has been shown to have material physiological effects on in vivo and in vitro animal tissue. As such, there has been extensive research and development in the use of weak, non-thermal electromagnetic field ("EMF") signals for promoting wound healing and tissue growth in humans. In particular, varied apparatuses with corresponding applicators have been developed for targeting specific biological pathways, such as nitric oxide upregulation, and parts of the human body, such as the head, knees, hips, chest, back, and bones for promoting healing from, inter alia, tissue inflammation, degenerative joint disorders, neurodegenerative disorders, traumatic injuries, surgeries, fractures, and the like. For example, U.S. Pat. No. 7,758,490 to Pilla et al., U.S. Pat. No. 7,896,797 to Pilla et al., U.S. Pat. No. 8,343,027 to DiMino et al., U.S. Pat. No. 8,415,123 to Pilla et al., U.S. Pat. No. 8,961,385 to Pilla et al., U.S. Pat. No. 9,320,913 to DiMino et al., U.S. Pat. No. 9,415,233 to Pilla et al., and U.S. Pat. No. 9,433,797 to Pilla et al., which are incorporated herein by reference, describe various PEMF apparatuses and corresponding regimens for treating human tissue—for injuries, surgery recoveries, and the like, at joints, bones, or soft tissue of various parts of the human body.

There is also a need for providing analogous PEMF treatment to animals, to affect similar pathways and to treat similar conditions as those enumerated above. For example, post-surgery treatments for promoting wound healing in veterinary applications are of particular interest. However, PEMF treatment in animals presents unique challenges that are not present in the human use context. For example, an animal patient may be reluctant to accept unusual contrivances for applying the PEMF and may resist any kind of applicator being placed proximate to the target tissue.

In addition, compliance in effecting the serial application of multiple treatments each requiring several minutes is difficult to sustain in humans or, especially, in an animal that would have to be restrained over long periods of time. Thus, direct adaptation of specifically-targeted human treatment devices, usually employing singular or paired coils in a wearable applicator, may not be optimal for treating certain conditions in humans and animals.

SUMMARY OF THE INVENTION

It is, therefore, an object of the invention to provide a PEMF treatment pad or bed that can accommodate a human or animal patient without necessarily alerting the patient of such treatment or requiring the patient to initiate a treatment cycle. In addition, it is an object of the invention to provide a PEMF treatment pad or bed that provides sufficient comfort for either a human or animal patient during treatment so that the patient may sustain an extended treatment period. It is a further object of the invention to provide a treatment pad or bed that may comprise treatment tracking functionality such that a human or animal patient may undergo extended treatment programs through multiple sessions, each of which may be initiated, tracked, paused, restarted, and logged simply by a detected proximity of the patient to the treatment bed or pad.

Treatment beds using plural coils for applying a uniform PEMF have been proposed in human use techniques. For example, U.S. Pat. No. 7,740,574 to Pilla et al., which is incorporated herein by reference, proposes a number of kinds of coil arrays for applying PEMF treatment in various contexts, such as a bed, a shoe, a hip sleeve, a head piece, a bra, and the like. Such coil arrays in, say, a treatment bed have been proposed with standard circular coils being placed uniformly across a mattress cover, or the like, without any detailed description on the particular arrangements of the coils or the corresponding effects of such arrangements.

According to an exemplary embodiment of the invention, a plurality of substantially-circular wire loops may be arranged in a squared or rectangular array, with each wire loop being coupled, separately or collectively, to one or more respective driving units that are controlled by one or more control devices and that are powered by a self-contained or external power source. According to an embodiment of the invention, each wire loop in the treatment bed array may comprise plural rounded indentations at portions proximate to the other wire loops such that the indentations of the respective wire loops form discontinuous circular patterns between adjacent wire loops in the array.

According to an embodiment of the invention, an apparatus for treating one or more subjects by applying one or more pulsed electromagnetic field (PEMF) signals thereto may comprise: one or more generator circuits each configured to generate a radio frequency (RF) signal; an array of plural loop antennas each coupled to a corresponding one of the one or more generator circuits, each loop antenna comprising a conductor coil having a generally circular shape with a plurality of rounded indentations in said generally circular shape; and an enclosure configured to house at least the array of plural loop antennas, said enclosure comprising a top surface configured to accommodate treated subjects, wherein each of the plurality of rounded indentations of each loop antenna is aligned with one of the plurality of rounded indentations of an adjacent loop antenna in the array.

According to an embodiment of the invention, the apparatus may further comprise one or more control circuits coupled to the one or more generator circuits, said one or more control circuits being configured to control activation of each of the plurality of generator circuits.

According to an embodiment of the invention, the one or more control circuits are coupled to, via one or more of a wired connection and a wireless connection, a computing apparatus, said computing apparatus configured to execute one or more programs adapted to generate instructions for the one or more control circuits.

According to an embodiment of the invention, each pair of the aligned rounded indentations in adjacent wire loops form a discontinuous substantially circular shape.

According to an embodiment of the invention, a diameter of the discontinuous substantially circular shape formed between adjacent wire loops is between approximately 2 inches and 6 inches.

According to an embodiment of the invention, a radius of the discontinuous substantially circular shape is approximately 1.45 inches.

According to an embodiment of the invention, each loop antenna coil has a radius of approximately 3.55 inches.

According to an embodiment of the invention, a method for treating a subject by applying one or more pulsed electromagnetic field (PEMF) signals thereto may comprise the steps of: providing an array of a plurality of loop antennas each coupled to a corresponding one or more generator circuits, each loop antenna comprising a conductor coil having a generally circular shape with a plurality of rounded indentations in said generally circular shape, in an enclosure configured to house at least the array of plural loop antennas, said enclosure comprising a top surface configured to accommodate the human subject or one or more animal subjects; detecting a presence of the human subject or one or more animal subjects; upon the condition of detecting a subject substantially on the top surface of the array, activating one or more of the generator circuits to generate a treatment signal to the corresponding one or more loop antennae.

According to an embodiment of the invention, the treatment signal is generated in accordance with a preprogrammed schedule.

According to an embodiment of the invention, the activating is further conditioned upon manual activation by a person or, in automatic mode, by the detection of the presence of the treated subject in the proximity of the array during a predetermined period of time during which the treatment signal is to be activated.

Wire loops of varying sizes and shapes may be used in accordance with the invention without departing therefrom. For example, wire loops of different shapes having smaller or larger dimensions may be used to form arrays of different sizes, with corresponding indentations being configured at portions of the arrays where adjacent wire loops come to close proximity with one another, with an optimal dimension of each indentation being between ¼ and ½, or approximately ⅓, of a corresponding dimension of the overall loop. In accordance with an embodiment of an invention, each wire loop may comprise one, two, or more cutouts (indentations) as long as the cutouts are oriented in sufficiently close proximity to a corresponding cutout of an adjacent loop.

An array of loop antennas having the rounded indentations in accordance with the invention generates a more uniform field for one or more PEMF signals across a treatment plane that is parallel to the array for a more consistent, therapeutically-effective treatment signal over substantially the entire area of the array, especially in the near field of approximately 0.1-1 inch, or about 0.5 inches, from a plane of the array.

Other features and advantages of the present invention will become readily apparent from the following detailed description and the accompanying drawings.

BRIEF DESCRIPTION OF THE DRAWINGS

FIG. 5B is a diagram illustrating a proximity detection assembly and process for the treatment pad/bed in accordance with an exemplary embodiment of the invention.

FIG. 5C is a block diagram illustrating the components of a radio frequency identification (RFID) device (FOB) for use with the treatment pad/bed in accordance with an exemplary embodiment of the invention.

FIG. 5D is a flow chart of a process of the RFID device (FOB) shown in FIG. 5C in a proximity detection process according to an exemplary embodiment of the invention.

FIG. 5E is a flow chart of a process of the control device shown in FIG. 5A in a proximity detection process according to an exemplary embodiment of the invention.

FIGS. 6B, 6C, 6D, and 6E are plan, side, and perspective views, respectively, of an air bladder treatment pad or bed in accordance with an exemplary embodiment of the invention.

FIGS. 7B and 7C are plan views of treatment pads/beds having circular wire loops and indented wire loops, respectively, conforming to the coil arrangement shown in FIG. 4C, with measurement points for results in Example 1.

The above and related objects, features and advantages of the present invention will be more fully understood by reference to the following, detailed description of the preferred, albeit illustrative, embodiment of the present invention when taken in conjunction with the accompanying figures, wherein:

DETAILED DESCRIPTION

Figure 1:
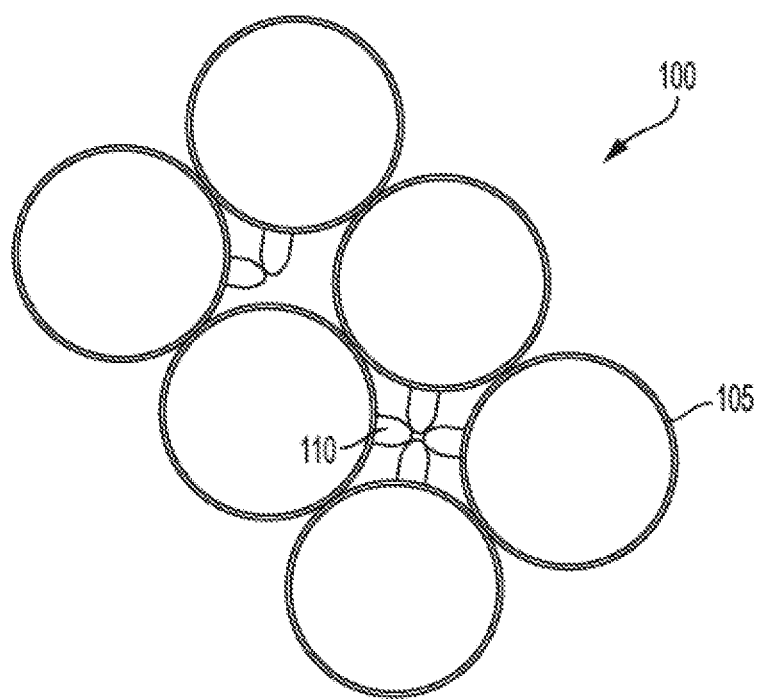
FIG. 1 is a plan view illustrating a testing array of six uniform circular coils for use in a treatment bed.

FIG. 1 is a plan view illustrating an array 100 of six uniform circular coils (hereinafter also referred to as wire loop) 105, each powered by a corresponding drive circuitry unit 110, for use in a treatment pad or bed. As shown in FIG. 1, the array of coils 105 may span approximately 15.03 inches in width—i.e., across two of the coils 105—and approximately 22.56 inches in length—i.e., across three of the coils 105. Accordingly, each coil 105 may be approximately 7.5 inches in diameter. Each of the coils 105 may be sized differently to accommodate differently sized arrays, pads, beds, patients, and corresponding treatment depth. According to an exemplary embodiment of the invention, each coil 105 may be approximately 5 to 8.5 inches in diameter. An optimal power output of each coil is preferably in the range of 100-300 mV (millivolts), or 110-250 mV, and is more preferably an average peak-to-peak amplitude of at least 120 mV.

Figure 2A:
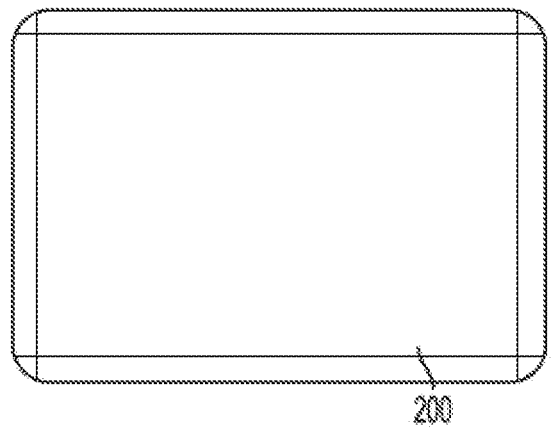
FIGS. 2A, 2B, 2C, and 2D are diagrams illustrating two of the array of FIG. 1 being placed side-by-side within a cushioned sleeve for a medium-sized treatment pad or bed.
Figures 2B, 2C:
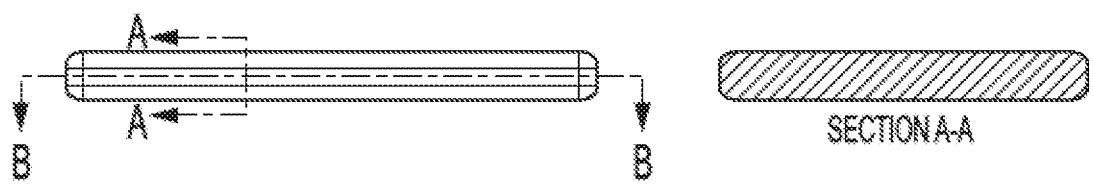
Figure 2D:
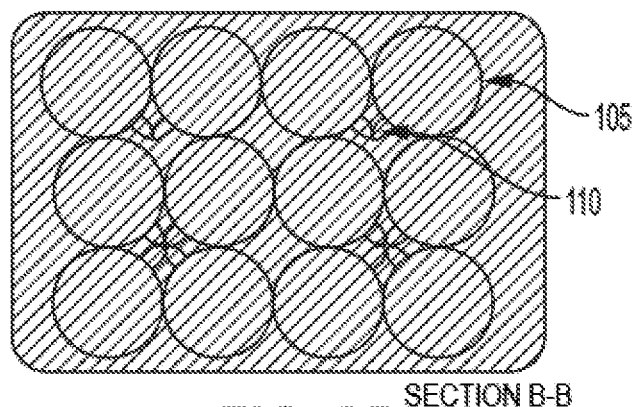

FIGS. 2A, 2B, 2C, and 2D are diagrams illustrating two of the array 100 of FIG. 1 being placed side-by-side within a cushioned sleeve for a medium-sized treatment bed 200. As shown in FIG. 2A, two of the arrays 100 of FIG. 1 may be arranged together to form a pad or bed 200 of a size of approximately 24.50 inches by 35.50 inches.

Figure 3A:
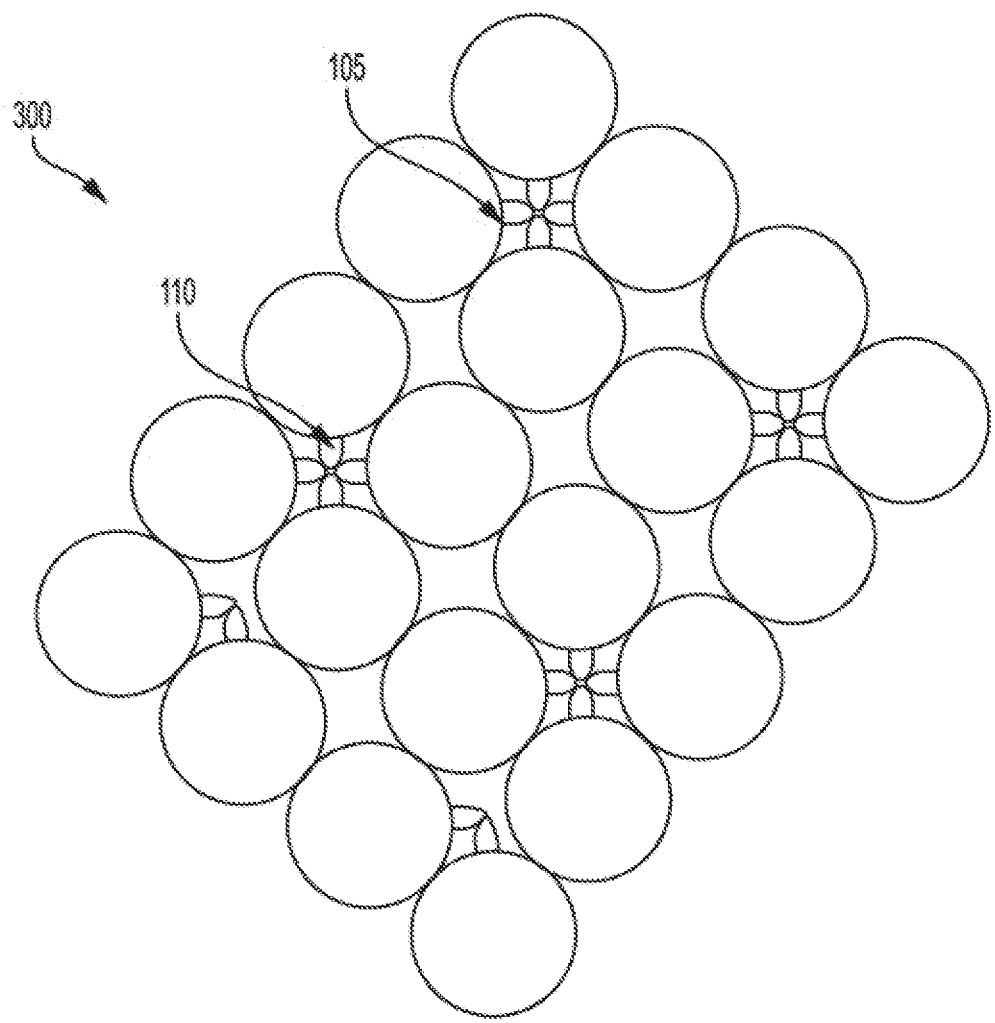
FIG. 3A is a plan view illustrating a larger testing array of twenty uniform circular coils.
Figure 3C:
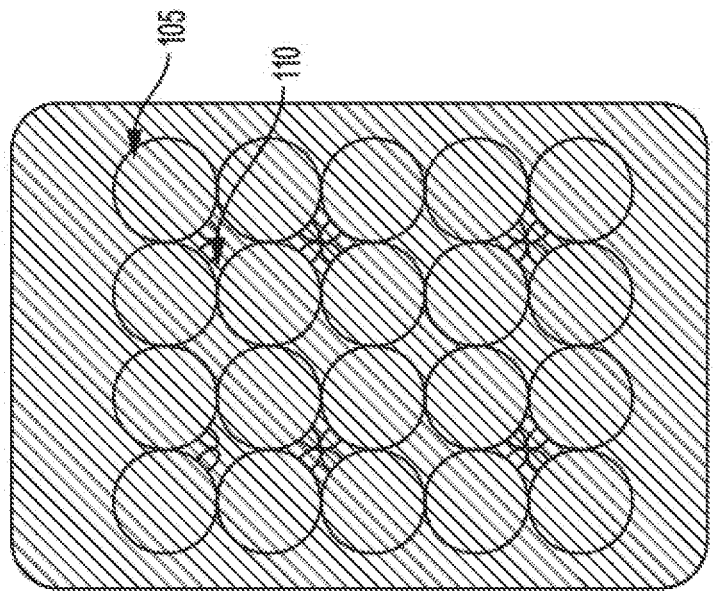
FIGS. 3B, 3C, 3D, and 3E are diagrams illustrating the array of FIG. 3A being placed within a cushioned sleeve for a larger-sized treatment pad or bed.
Figure 3E:
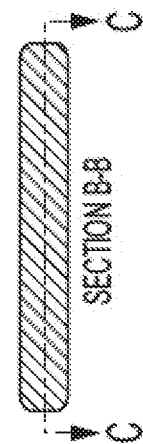
Figure 3B:
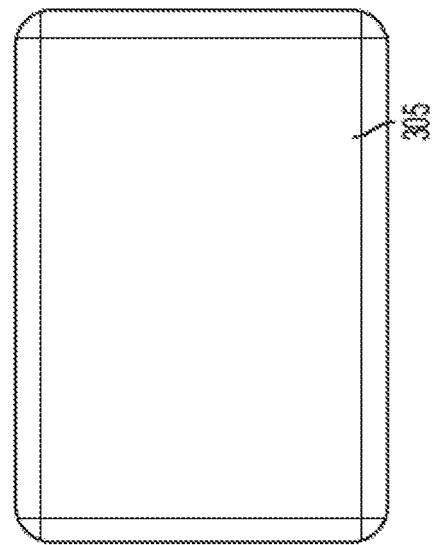
Figure 3D:
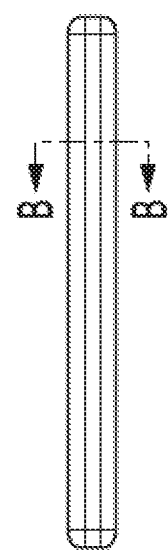

Correspondingly, FIG. 3A is a plan view illustrating a larger array 300 of twenty uniform circular coils and FIGS. 3B-3E are diagrams illustrating the array 300 of FIG. 3A being placed within a cushioned sleeve for a larger-sized treatment pad or bed 305. Again, each circular coil 105 may have a diameter of approximately 5 to 8.5 inches—preferably 6 to 7.5 inches for a depth of tissue penetration of approximately 4 to 5 inches—with the optimal output for each coil being approximately 130-180 mW. FIGS. 3A-3E show an example of a treatment pad or bed 305 that is formed by coils of about 7.5 inches in diameter and, thus, forming a pad or bed 305 of approximately 32.60 inches by 50 inches, as shown in FIG. 3B, that houses an array of approximately 30.28 inches by 37.67 inches, as shown in FIG. 3A.

Figure 5A:
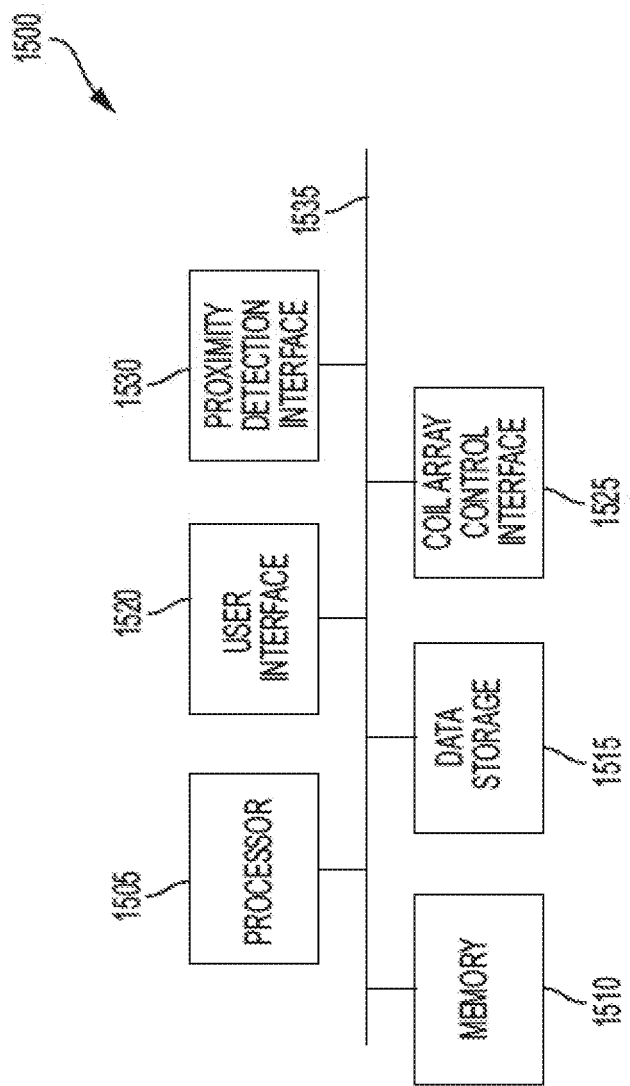
FIG. 5A is a block diagram illustrating the components of a control device for a treatment pad/bed in accordance with an exemplary embodiment of the invention.

According to an embodiment of the invention, the drive circuitry units 110 may collectively be coupled to a power source, such as a battery, a household A/C power source via a power converter, and the like. The drive circuitry units may also comprise control functionality and may be coupled, individually or collectively, to another control device (hereinafter also referred to as a controller, controller device, or control apparatus), as shown in FIGS. 5A and 5B and described in further detail below. The control device may provide instructions for signal generation by the drive circuitry units 110 via the coils 105, as described in further detail below.

According to an embodiment of the invention, the coils may be place within a cushioned sleeve between two cushion layers that are made from, for example, foam rubber and the like. Alternatively, the coils may be embedded within a soft polymer enclosure to one side of a cushion layer. Depending upon the treatment depth needed for a patient, the treatment surface for such a treatment pad/bed may be on the polymer enclosure side or the cushion layer side.

In accordance with an exemplary embodiment of the invention, drive circuitry units 110 may each comprise a tuning element that is a circuit used to adjust and match an impedance of a PEMF short wave radio frequency generator to an emitter applicator—i.e., a corresponding one of the wire loops 105—post assembly. The post assembly impedance adjustments compensate for variability in standard components to optimize radio frequency power output while conforming with ISM bandwidth regulations. FDA-cleared PEMF devices use 27.12 MHz as the standard carrier frequency. According to an embodiment of the invention, for more precise frequency control, a 27.12 MHz crystal may be used.

Industrial Scientific and Medical Equipment (ISM) frequencies are those frequencies allocated by the Federal Communications Commission pursuant to 47 CFR 18.301 for specific applications based on a target frequency and allowed bandwidth. The FDA has recognized the 27.12 MHz frequency (±163.0 kHz) for diathermy devices on a preamendments substantial equivalency basis. In the class of PEMF devices, cleared by the FDA, the 27.12 MHz is the standard carrier frequency.

Figure 3F:
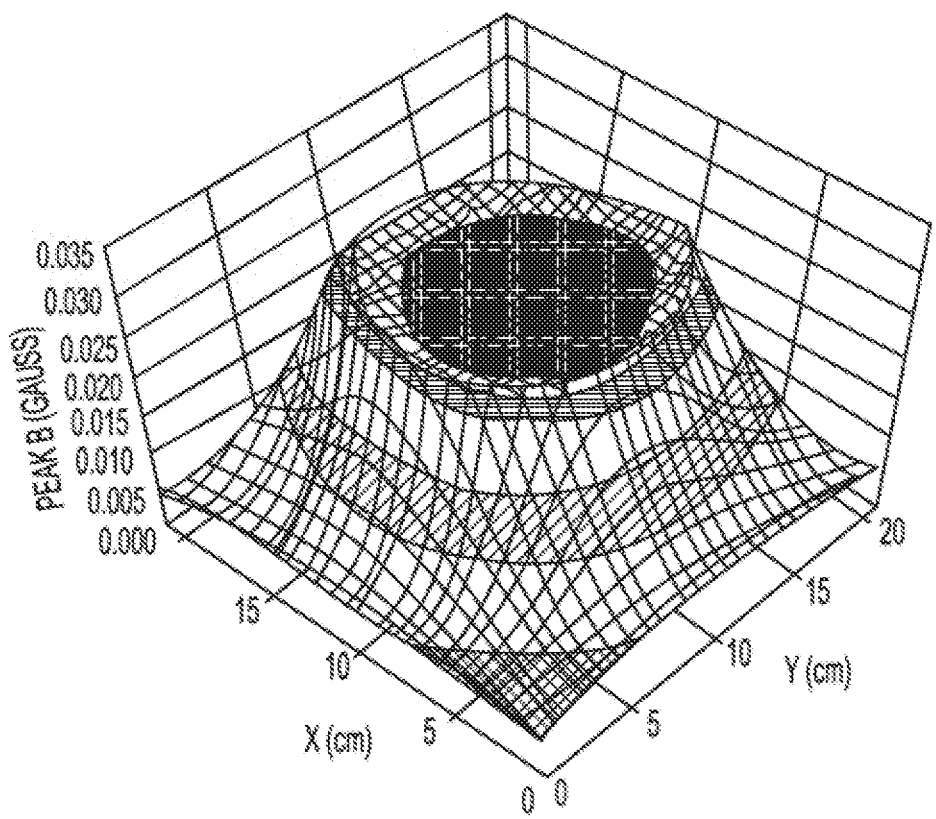
FIG. 3F is a three-dimensional graph showing the amplitude of a PEMF field generated by a singular circular wire loop measured at approximately two (2) centimeters from a plane of the wire loop.

FIG. 3F illustrates a measured PEMF field generated by a circular wire loop, in correspondence with wire loops 105 shown in FIGS. 1, 2D, 3A, and 3C. The distribution of a resultant peak field may be on a plane parallel to, and at 1 cm from, the plane of a circular loop antenna. As shown in FIG. 3F, the field amplitude is highest within the boundary of the loop coil, as expected for the propagation of an electromagnetic field from a circular loop antenna into a cylindrical saline tissue phantom in the near field.

Thus, in the near field of approximately between 0.1 and 1 inch from the plane of an array of circular wire loops, a PEMF signal profile may exhibit a relatively wide range of amplitudes across the array, accentuated by the amplitude profile illustrated in FIG. 3F for each of the wire loops in the array.

In the interest of improving the near field performance, an array of differently shaped wire loops may be implemented to yield a more uniform signal profile.

Figure 4A:
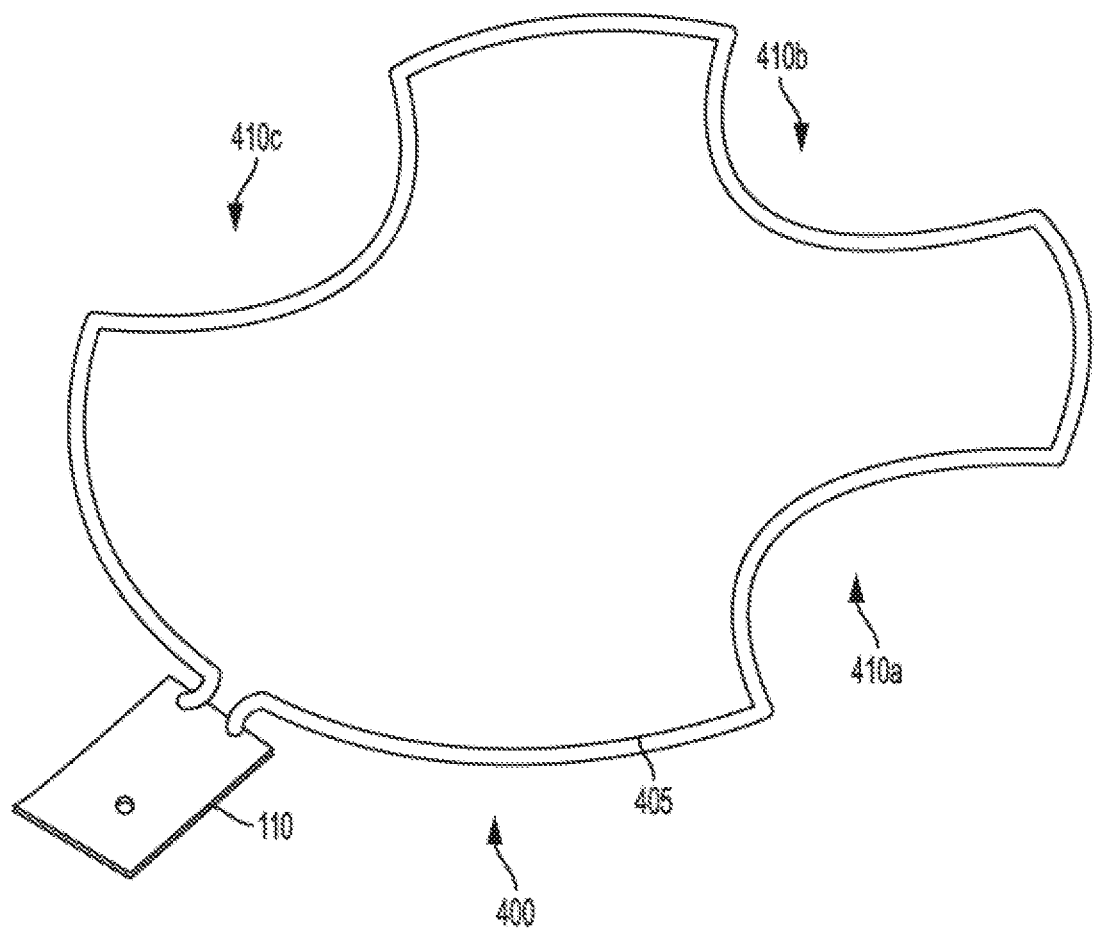
FIG. 4A is a perspective view of a singular wire loop coupled to a generator circuit in accordance with an exemplary embodiment of the invention.

FIG. 4A is a perspective view of a singular wire loop assembly 400 comprising a wire loop (coil) 405 coupled to a generator circuit 110 in accordance with an exemplary embodiment of the invention. As shown in FIG. 4A, a wire loop (coil) 405 according to the invention may comprise a generally circular shape with three rounded indentations 410a, 410b, and 410c that correspond to positions of other wire loops when placed in an array for a treatment bed. According to an embodiment of the invention, each wire loop (coil) 405 may have a different number of rounded indentations depending upon an arrangement an array of such coils 405—for example, as illustrated in FIGS. 4D and 4E and as described in further detail below.

Figure 4B:
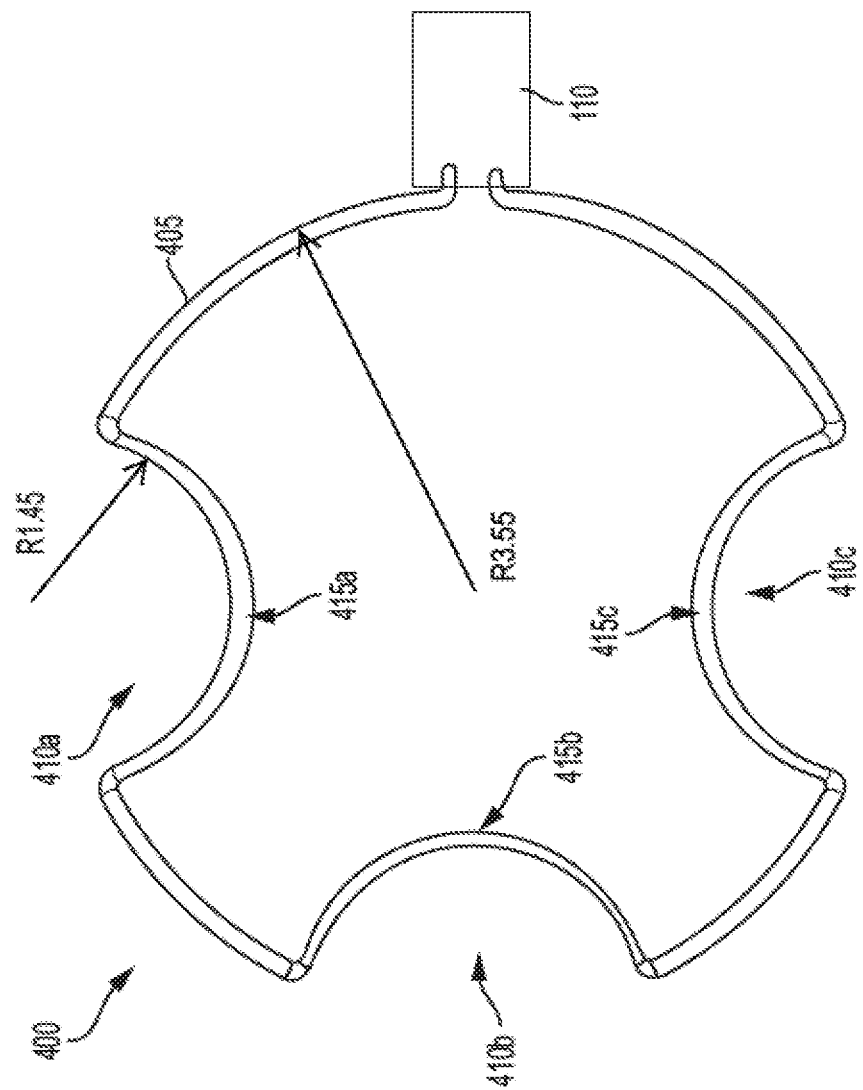
FIG. 4B is a plan view of a singular wire loop coupled to a generator circuit in accordance with an exemplary embodiment of the invention.

FIG. 4B is a plan view showing the dimensions, in inches, of the singular wire loop assembly 400 according to an exemplary embodiment of the invention. Each wire loop 405 of an array according to the invention may be approximately 5 to 8.5 inches in diameter—or preferably, 6 to 7.5 inches in diameter. For example, as shown in FIG. 4B, wire loop 405 may have a radius of approximately 3.55 inches with three rounded indentations 410a, 410b, and 410c that correspond to respective rounded indentations 410 of adjacent wire loops 405 in an array. As further illustrated in FIG. 4B, two rounded indentations 410 of respective adjacent wire loops 405 may together form a generally circular shape having a radius of approximately 1 to 2 inches—for example, approximately 1.45 inches. For example, a distance from a nadir (or center point) 415a, 415b, and 415c of respective rounded indentations 410a, 410b, and 410c to a corresponding point in a rounded indentation 410 of an adjacent wire loop 405 may define a diameter of the (discontinuous) generally circular shape, which will be described in further detail below. According to an exemplary embodiment of the invention, the generator circuit (which may be referred to as a drive circuitry unit) 110 may be enclosed in a housing with an independent power source, such as a battery, or a connector adaptable to receiving power from an external source. In addition, the housing of the generator circuit 110 may be integrated to comprise: a signal generator configured to generate a signal, including a treatment waveform, for the wire loop; a signal amplifier with a tuning element for amplifying the generated signal to be applied to the wire loop; and an impedance matching circuit and a corresponding tuning element coupled to either or both of the signal amplifier and the wire loop. A controller may be incorporated in the housing or otherwise coupled to the generator circuit 110 through a wired or wireless connection.

Figure 4C:
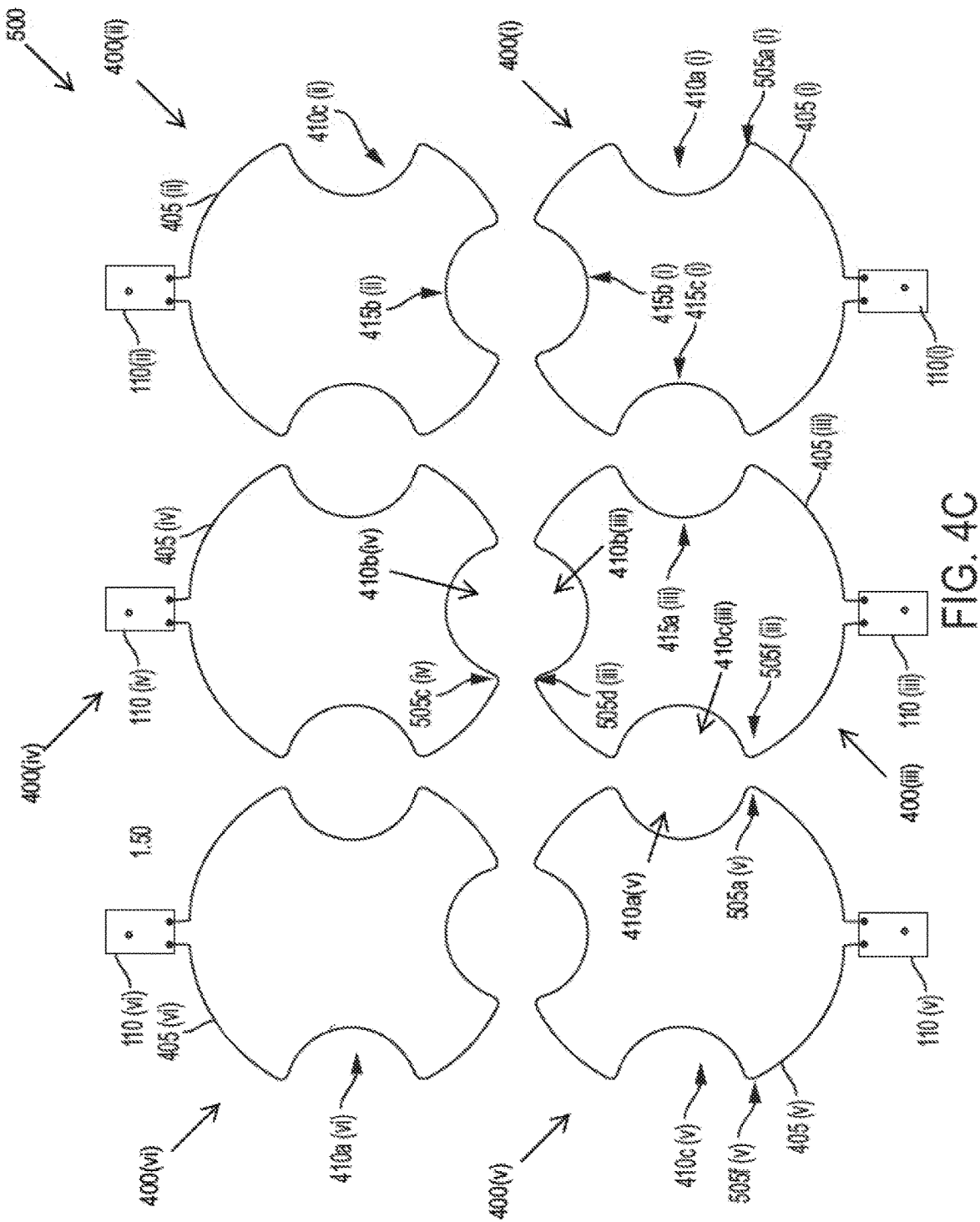
FIG. 4C is a plan view of an array of the wire loops shown in FIGS. 4A and 4B in accordance with an exemplary embodiment of the invention.
Figure 4D:
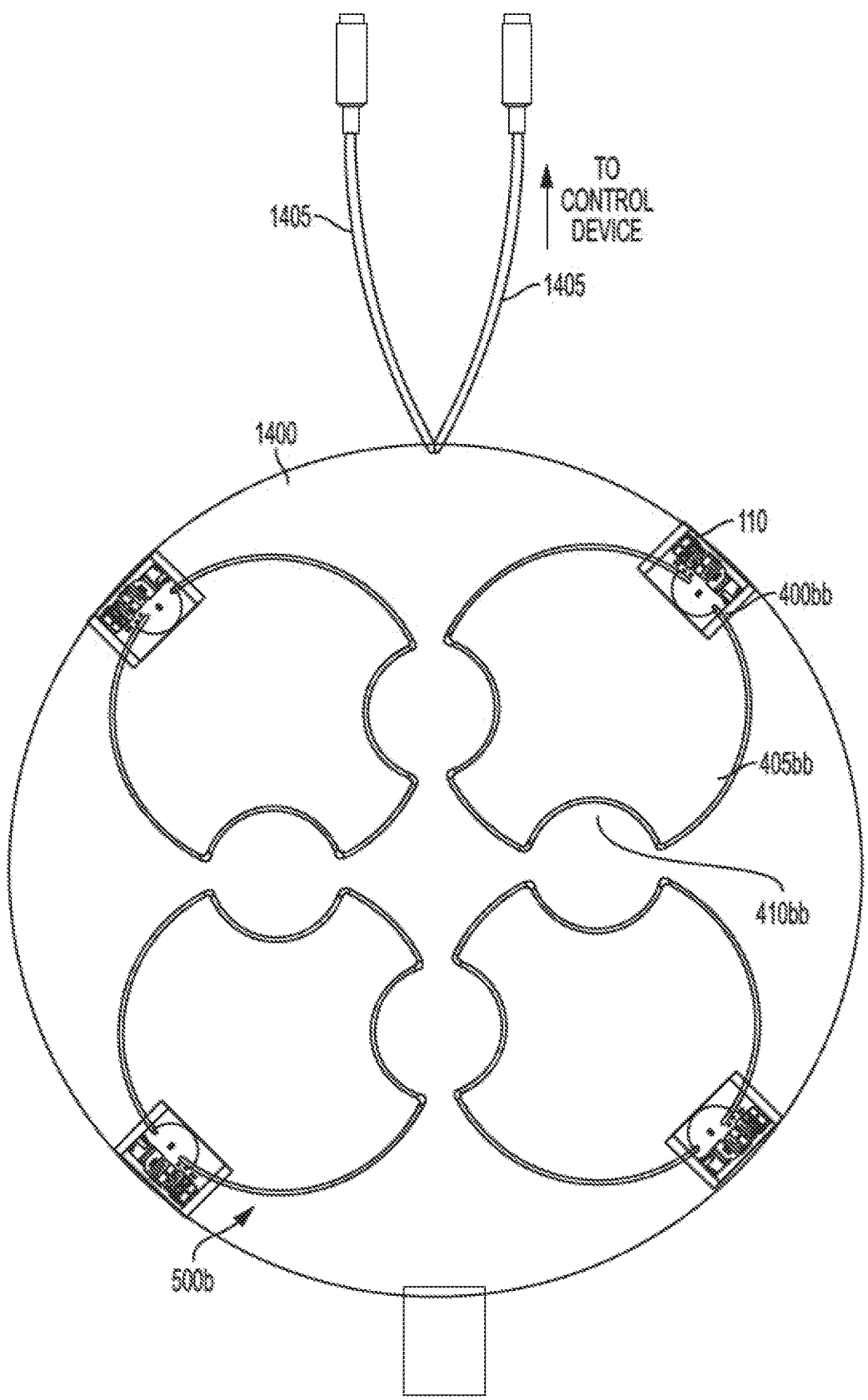
FIG. 4D is a plan view of a treatment pad/bed incorporating a two (2) by two (2) array of wire loops having corresponding rounded indentations according to another exemplary embodiment of the invention.
Figure 4E:
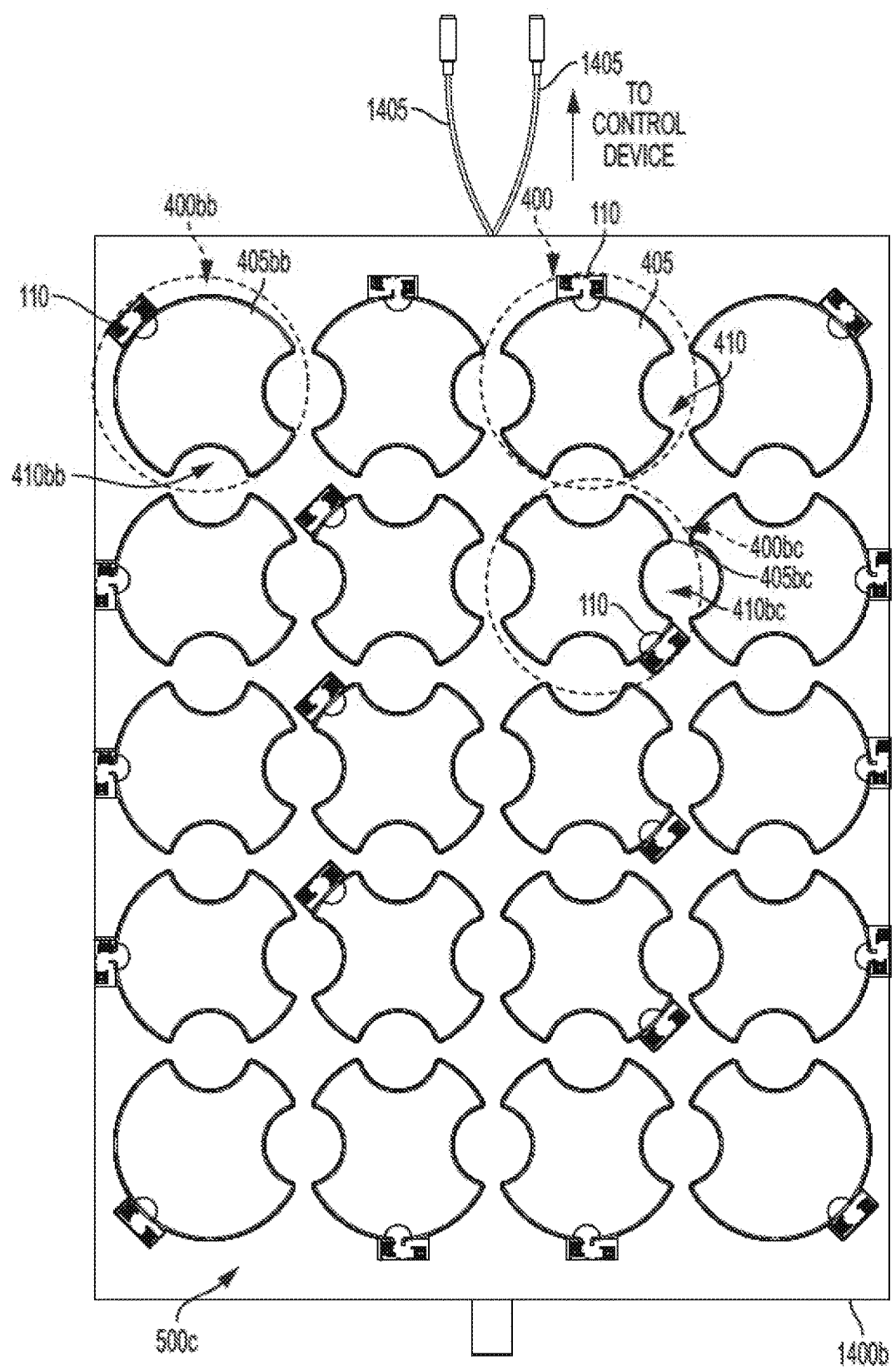
FIG. 4E is a plan view of a treatment pad/bed incorporating a four (4) by five (5) array of wire loops having corresponding rounded indentations according to yet another exemplary embodiment of the invention.

FIG. 4C is a plan view of array 500 showing dimensional features of the wire loop assemblies 400, with wire loops (coils) 405 and their respective rounded indentations 410 according to an exemplary embodiment of the invention. It is noted that FIG. 4C illustrates the wire loop assemblies 400 of array 500 each having a structure corresponding to the structure shown in FIGS. 4A-B with numerals (i)-(vi) denoting the elements of each of the six respective wire loop assemblies 400(i)-(vi) in array 500 in correspondence with the individual structural elements shown in FIGS. 4A-B. (Some of the corresponding individual elements of wire assemblies 400(i)-(vi) are not explicitly marked in FIG. 4C due to space constraints and for clarity) As shown in FIG. 4C, respective wire loop assemblies 400(i)-(vi) having respective generator circuits 110(i)-(vi) and wire loops (coils) 405(i)-(vi) that may be aligned to form array 500. The rounded indentations (selectively denoted by 410a, 410b, or 410c with a corresponding (i)-(vi) for each respective wire loop 405(i)-(vi), for example, 410a(i), 410c(ii), 410b(iii), 410c(iii), 410b(iv), 410a(v), 410c(v), and 410a(vi) referenced in FIG. 4C) of adjacent wire loops 405(i)-(vi) may form a (discontinuous) substantially circular shape having a diameter in a range of approximately 2 to 4 inches, or about 3 inches. For example, as shown in FIG. 4C, the distance between a nadir 415b(i) of wire loop 405(i) and a nadir 415b(ii) of wire loop 405(ii)—thus, reflecting a diameter of the generally circular shape formed by the respective rounded indentations 410b(i) and 410b(ii)—may be approximately 2 to 4 inches, or about 3 inches. Similarly, the distance between a nadir 415c(i) of wire loop 405(i) and a nadir 415a(iii) of wire loop 405(iii)—thus, reflecting a diameter of the generally circular shape formed by the respective rounded indentations 410c(i) and 410a(iii)—may be approximately 2 to 4 inches, or about 3 inches. Each wire loop 405(i)-(vi) may, itself, have a diameter of approximately 5 to 8.5 inches, or about 6 to 7.5 inches, or more preferably about 6 inches, with adjacent wire loops 405 being approximately 0.1 to 1 inch apart, or about 0.75 inches apart, at their respective closest points that coincide with the beginnings and ends of the rounded indentations 410. For example, as shown in FIG. 4C, wire loops 405(iii) and 405(iv) may be approximately 0.1 to 1 inch, or about 0.75 inches, from each other between points 505d(iii) and 505c(iv) thereof—these points 505d(iii) and 505c(iv) representing bending points towards rounded indentations 410b(iii) and 410b(iv) of wire loops 405(iii) and 405(iv), respectively. Similarly, wire loops 405(iii) and 405(v) may be approximately 0.1 to 1 inch, or about 0.75 inches from each other between points 505f(iii) and 505a(v) thereof—these points 505f(iii) and 505a(v) representing bending points towards rounded indentations 410c(iii) and 410a(v) of wire loops 405(iii) and 405(v), respectively.

Each rounded indentation—for example, 410a(i), 410c(ii), 410b(iii), 410c(iii), 410b(iv), 410a(v), 410c(v), 410a(vi) referenced in FIG. 4C—may, again, be of a generally circular shape with a respective nadir—for example, 415b(i), 415c(i), 415b(ii), 415a(iii) referenced in FIG. 4C—at approximately ⅓ of the diameter of the corresponding wire loop 405(i)-(vi), or approximately 1 to 2 inches (or about 1.5 inches) from a corresponding circumference point of the wire loop 405(i)-(vi). Accordingly, as further shown in FIG. 4C, an array 500 may be approximately 20.58 inches—as measured between points 505a(i) and 505f(v) of wire loops 405(i) and 405(v)—by 17.71 inches—as measured between respective ends of generator circuits 110(i) and 110(ii). In accordance with an exemplary embodiment of the invention, an amplitude of the PEMF signal at points on a plane that is parallel to—and at a distance of approximately 0.1-1 inch, or about 0.5 inches, from—a plane of the array 500 of wire loops (coils) 405(i)-(vi) is preferably in the range of 100-300 mV (millivolts), or 110-250 mV, and is more preferably an average peak-to-peak amplitude of at least 120 mV within the above-prescribed dimensions of each loop, as shown in FIG. 4C, and with respective characteristics conforming to the measured field illustrated in FIG. 5B according to the dimensions of the respective loops.

FIG. 4D is a plan view of a treatment pad/bed 1400 housing an array 500b of wire loop assemblies 400bb, with wire loops (coils) 405bb and their respective rounded indentations 410bb according to an exemplary embodiment of the invention. As shown in FIG. 4D, array 500b may have two-by-two (2×2) loops 405bb, with respective rounded indentations 410bb, to form a circular treatment pad/bed 1400 for, say, a smaller animal. As shown in FIG. 4D, loops 405bb may each comprise two rounded indentations 410bb that are aligned with one another around a central portion of array 500b such that loops 405bb retain their generally circular circumferences around the periphery of array 500b and, correspondingly, the treatment pad/bed 1400. As shown in FIG. 4D, treatment pad/bed 1400 may comprise one or more connectors 1405 for connecting to a control device.

FIG. 4E is a plan view of a treatment pad/bed 1400b housing an array 500c of wire loop assemblies 400, 400bb, and 400bc, with wire loops (coils) 405, 405bb, and 405bc and their respective rounded indentations 410, 410bb, and 410bc according to an exemplary embodiment of the invention. As shown in FIG. 4E, array 500c may have four-by-five (4×5), or twenty (20), loops comprising loops 405, 405bb, 405bc (for example, ten (10) wire loops 405, four (4) wire loops 405bb, and six (6) wire loops 405bc), with respective rounded indentations 410, 410bb, 410bc, to form a larger rectangular treatment pad/bed 1400b for, say, a human patient or a larger animal. As further shown in FIG. 4E, loops 405, 405bb, and 405bc may have different respective numbers of rounded indentations 410, 410bb, and 410bc that are aligned with one another at adjacent portions of the loops 405, 405bb, and 405bc, where the loops 405 and 405bb retain their generally circular circumferences around the periphery of array 500c and, correspondingly, the treatment pad/bed 1400b. As shown in FIG. 4E, treatment pad/bed 1400b may comprise one or more connectors 1405 for connecting to a control device.

As described above, each loop 405, 405bb, and 405bc may be sized to approximately 5-8.5 inches in diameter where the aligned adjacent indentations 410, 410bb, and 410bc may form respective discontinuous "loops" of generally circular shapes that are sized to approximately 2.5-4.8 inches in diameter. As illustrated in FIGS. 4D and 4E, arrays 500b and 500c may incorporate one or more linking connectors 1405 for coupling to one or more control devices such that control signals may be sent to the respective driving units 110 of the respective loops 405, 405bb, and 405bc for generating PEMF treatment signals across arrays 500b and 500c.

In accordance with an exemplary embodiment of the invention, a treatment pad or bed incorporating an array as shown in FIG. 4C—also treatment pads or beds that are arranged as illustrated in FIGS. 2A-2D, 3A-3E, and 4D-4E—may be used to treat a subject on a top or bottom surface (such as an equine wrap) of the treatment pad or the top surface of a treatment bed.

The treatment pad or bed may include a RFID ("Radio-frequency identification") sensing assembly for detecting the presence of a subject on top or bottom of the treatment pad or top of the treatment bed in order to initiate treatment. In accordance with an exemplary embodiment of the invention, the RFID sensing assembly may comprise location sensing elements in cooperation with, say, a RFID chip, which may be embedded in, for example, a key fob, a bracelet, a collar—or a fob attached to the collar—and the like, for a human or animal subject, whereby treatment is initiated upon sensing the proximity of a predetermined identification (RFID) tag. Correspondingly, each of the treatment coils and their respective control circuits may be collectively or individually activated and controlled, for example, by the sensed proximity of the RFID tag. For example, treatment may be conditioned upon a predetermined period of no detected movement from the subject. In addition, treatment regimens may comprise any programs energizing one or more of the wire loops 405 near-simultaneously or sequentially according to a predetermined order or a pseudo random order for respective durations, which can be constant or variable according to treatment needs, subject size, and the like. Multiple wire loops 405 may also be alternately energized according to a preprogrammed order or a pseudo-random order with constant or variable durations. Other suitable means can also be utilized for automatically or manually controlling the application of PEMF treatment energy via the wire loops 405 near-simultaneously or sequentially in accordance with predetermined treatment regimens. Advantageously, an array 500 having wire loop antennas 405 with respective rounded indentations 410, as described above, provides for more effective treatment regimens that energize the wire loops 405 near-simultaneously resulting in a more uniform field across the array 500. However, as noted above, other regimens may be appropriate for particular treatment types and objectives.

FIG. 5A is a block diagram illustrating components of a controller (control device) for connecting to and controlling a treatment pad or bed embodying a coil array in accordance with an exemplary embodiment of the invention.

As shown in FIG. 5A, controller 1500 may comprise a processor 1505, a memory unit 1510, a data storage 1515, a user interface 1520, a coil array control interface 1525, and a proximity detection interface 1530 that are connected to one another through a communication bus 1535. Memory unit 1510 and data storage unit 1515 may comprise one or more devices storing and providing programmed instructions to processor 1505 for execution. Memory and data storage devices may be removable or non-removable and may include nonvolatile media and non-transitory media, a Random Access Memory (RAM), a Programmable Read Only Memory (PROM), an Erasable Programmable Read Only Memory (EPROM), a Flash EPROM, any other memory chip or cartridge, or any other tangible medium from which a processor (1505) can read instructions.

As shown in FIG. 5A, controller 1500 may comprise a processor device 1505 coupled to one or more of a memory 1510 and a data storage device 1515 for storing and providing program instructions to be executed by the processor device 1505 in facilitating treatment regimens associated with the coil array described above via a coil array control interface 1525. In accordance with an exemplary embodiment of the invention, user interface 1520 may comprise one or more display and/or audio/visual indicator devices for indicating an operational status of the coil array and, correspondingly, treatment pad/bed. The user interface 1520 may further comprise one or more input devices for receiving a user input for powering on/off the controller 1500 and treatment apparatus, selecting respective treatment programs, programming the controller 1500 for different treatment procedures, and the like. As an example, user interface 1520 may comprise one or more LED indicators, one or more push buttons, a keypad, and the like.

Coil array control interface 1525 may comprise a connector for connecting to, for example, connector 1405 shown in FIGS. 4D and 4E, and for controlling a power supply and/or signal generator(s)—in drive units 110—of a coil array to effectuate a selected treatment regimen(s) in accordance with a user selection through user interface 1520 and/or a pre-programmed regimen. Accordingly, control signals may be transmitted to respective signal generators in drive units 110 of respective coils in a coil array (e.g., 500, 500b, and 500c) via coil array control interface 1525, thereby causing the respective coils to transmit treatment signals in accordance with program regimens executed by processor 1505.

In accordance with an exemplary embodiment of the invention, controller 1500 may comprise a proximity detection interface 1530 for communicating with one or more devices (e.g., an RFID FOB) in order to detect a proximity of a treatment subject in relation to a treatment pad/bed. As described above, proximity detection may be effectuated by using one or more RFID devices for indicating the location of a treatment subject.

Referring now to FIGS. 5B-5E, a proximity detection technique according to an exemplary embodiment of the invention will be described. FIG. 5B illustrates an example of an RFID fob 1600 being incorporated in a pet collar with internal detectors for sensing the RF signals 1605 generated by a coil array 500 housed within a treatment pad/bed to thereby determine the proximity of the treatment subject 1610 from the coil array 500. FIG. 5B shows coil array 500 for illustrative purposes only and the describe technique is equally applicable to treatment pads/beds incorporating, for example, arrays 500b and 500c shown in FIGS. 4D and 4E. The RFID device 1600 may also be worn as a wearable device by a human subject on a wrist band, necklace, ankle band, or the like. Alternatively, the RFID device 1600 may be incorporated by a general purpose wearable device with a proximity detection software program application ("app"), with an antenna and receiver tunable to the 27.120 MHz frequency of RF signals 1605. As shown in FIG. 5B, RFID device 1600 may detect the RF signals 1605 and may, upon detecting the signals 1605, communicate with controller 1500 via wireless communication, for example by the Bluetooth protocol, as described in further detail below.

FIG. 5C illustrates a configuration of a RFID device (FOB) 1600 in accordance with an exemplary embodiment of the invention. As shown in FIG. 5C, the FOB 1600 may comprise a PEMF antenna 1700 configured to detect the PEMF signals 1605 shown in FIG. 5B transmitted from the coil array 500 (500*b* or 500*c*). The PEMF antenna 1700 may be coupled to a receiver 1705 tuned to the 27.120 MHz frequency of the PEMF signals 1605. The receiver 1705 may be coupled to a microcontroller (MCU) 1710 that may comprise a wireless communication interface, such as a Bluetooth interface, for communicating with controller 1500 shown in FIGS. 5A and 5B. For example, the MCU 1710 may be a lower energy Bluetooth device for generating and receiving Bluetooth signals via a Bluetooth (BLE) antenna 1715. The receiver 1705 and MCU 1710 may be powered by an integrated power source 1720 of the RFID device 1600, such as a battery, which may be rechargeable through a wired or wireless coupling to an external power source.

FIG. 5D is a flowchart illustrating a process 1800 executed by the RFID device 1600 shown in FIGS. 5B and 5C. As shown in FIG. 5D, at step S1805 MCU 1710 determines whether receiver 1705 has received an RF signal at the tuned 27.120 MHz frequency that is above a predetermined amplitude threshold or within a predetermined amplitude range. In accordance with an exemplary embodiment of the invention, once a 27.12 MHz signal at approximately between 1 mV and 255 mV is received by the receiver 1705, MCU 1710 proceeds to step S1810 and transmits a signal incorporating an identification of the RFID device 1600 and the RF level of the received signal to controller 1500 via the BLE antenna 1715. As an example, the identification of the RFID device 1600 may be indicated by a plurality of databits that are unique to the RFID device 1600, such that plural RFID devices may be identified by the controller 1500 and respective treatment regimens corresponding to the respective plural RFID devices may be tracked, recorded, and logged at the controller 1500.

FIG. 5E is a flowchart showing a process 1900 of the controller 1500 that detects the proximity of the RFID device 1600 and, in turn, the treatment subject 1610 in correspondence with the process 1800 shown in FIG. 5D according to an exemplary embodiment of the invention. As shown in FIG. 5E, controller 1500 starts a treatment cycle and transmits one or more instruction signals to the coil array 500 to begin delivering PEMF therapy signals 1605, at step S1905. In accordance with an exemplary embodiment of the invention, a start of a treatment cycle may comprise a predetermined number of signal bursts for PEMF therapy signals 1605 such that RFID device 1600 may detect the signal bursts. The start of the treatment cycle may be automatically triggered upon powering on controller 1500 or it may be manually toggled via user interface 1520. In accordance with an exemplary embodiment of the invention, step S1905 may be executed with or without a timer for tracking treatment time. As an example, controller 1500 may, by default, trigger a treatment timer at step S1905 for a particular subject 1610 if only one RFID device 1600 has been registered and/or logged by the controller 1500 in past treatment cycles.

Next, at step S1910, controller 1500 listens for a BLE signal from one or more FOB RFID devices (1600). When a BLE signal is received, controller 1500 proceeds to step S1915, where the received FOB RF level is determined by reading the information in the received BLE signal. The received FOB RF level is, then, compared to a predetermined threshold corresponding to a distance from the coil array 500. If the RF signal exceeds the threshold reflecting the RFID device (1600) being likely within the perimeter of the coil array 500 ("Y"), controller 1500 proceeds to step S1920 and determines whether a treatment time for the identified RFID device (1600) and subject (1610) has elapsed. As described above, a treatment timer for a treatment regimen associated with an RFID (1600) identification may or may not be triggered at the outset of process 1900. As an example, a treatment timer may be triggered at step S1905 if only one RFID device 1600 has been registered and/or logged by the controller 1500 in past treatment cycles. Alternatively, a treatment timer may not be started until a positive determination at step S1915 ("Y") is returned where a particular RFID device (1600) has been identified to be above threshold, thereby indicating a subject (1610) to be within a treatment perimeter. Such a delayed start to a treatment timer may be particularly appropriate when controller 1500 is monitoring more than one RFID device (1600) and corresponding subject (1610). For example, if a treatment regimen has already begun for a treatment subject (1610) assigned to a particular RFID device (1600), controller 1500 may restart a tracking timer corresponding to the treatment regimen and continue tracking the treatment from, say, a previous session.

As described above, controller 1500 then proceeds to step S1920 to determine whether a treatment time has 705 elapsed. If the treatment time has not exceeded a predetermined duration that corresponds to a treatment regimen for the subject associated with the RFID identification ("N"), then controller 1500 returns to step S1910 to repeat the BLE signal listening and signal strength determination, step S1915. Accordingly, controller 1500 repeatedly determines whether the treatment subject (1610) remains within the treatment zone of array 500 so that any time the treatment subject (1610) exits the treatment zone—i.e., the received FOB RF level is below threshold, or "N" at step S1915—the PEMF therapy signal 1605 may be stopped, at step S1925, and, corresponding, the treatment tracking timer may be paused.

If the treatment subject (1610) remains within the treatment zone for a sufficient duration that the treatment regimen is completed, i.e., the treatment time is elapsed ("Y" from step S1920), controller stops the PEMF therapy (step S1925) and ends the treatment cycle.

The controller 1500, thus, keeps track of the treatment time and subject location while delivering the PEMF signals 1605 via coil array 500. If a subject leaves the treatment zone, the PEMF signals 1605 may be interrupted, as described above. According to an exemplary embodiment of the invention, the controller 1500 may instruct coil array 500 to transmit intermittent PEMF signals 1605 at intervals with durations of between approximately 15 to 25 seconds, preferably at about 20 seconds, each minute to continuously detect for a return of the treatment subject 1610. A semi-permanent end to a treatment cycle may be effectuated after a predetermined number of cycles—say, 45—has been completed without detecting a return of a treatment subject 1610.

Figure 6A:
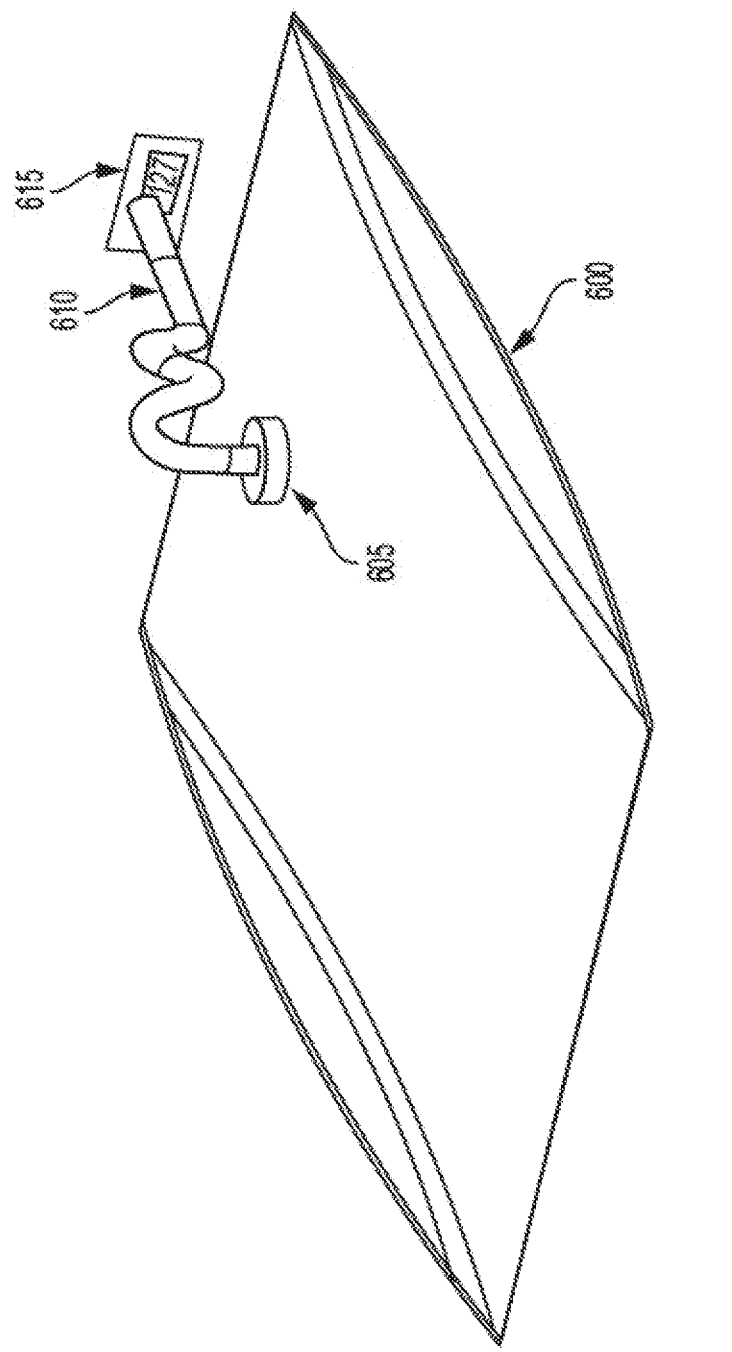
FIG. 6A is a perspective view of an air bladder pad or bed for accommodating the array of wire loops to form an animal treatment bed in accordance with an exemplary embodiment of the invention.
Figure 6E:
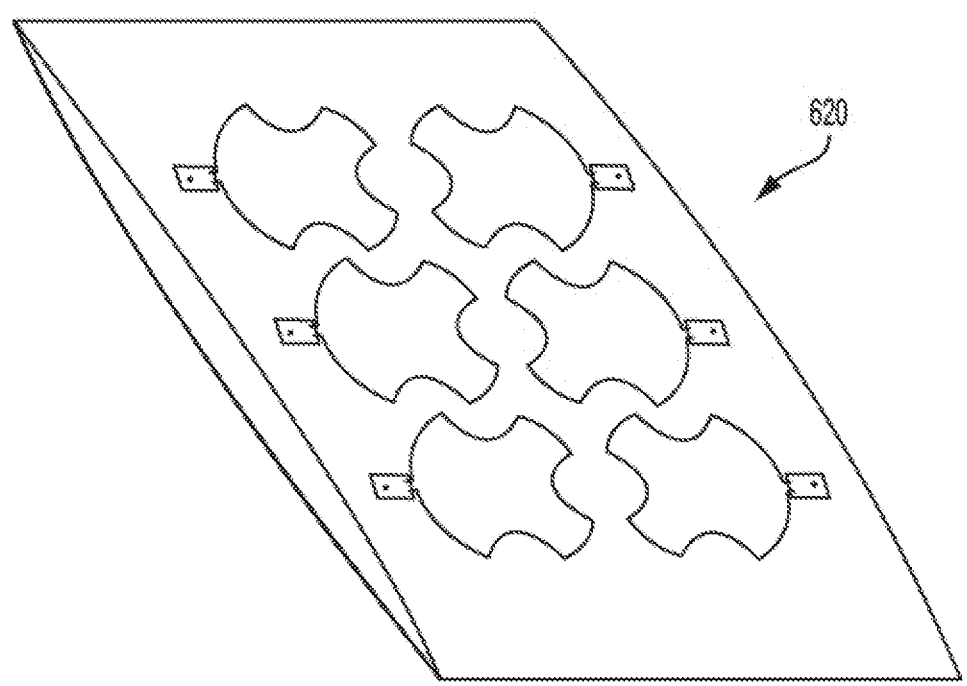

In accordance with an alternative exemplary embodiment, the treatment pad or bed may incorporate an air bladder that is coupled to an air pressure toggle that triggers activation upon a weight of a subject increasing the pressure on the air bladder. FIG. 6A illustrates an inflatable bladder 600 for forming a treatment bed 605 incorporating array 500, as shown in FIGS. 6B-6E. According to an exemplary embodiment of the invention, bladder 600 may include an air intake/outtake 605 coupled to a pumping/air pressure detection and maintenance device 615 through an airway (or hose) 610. The air pressure detection and maintenance device 615 may maintain an internal pressure of approximately 10 psi for bladder 600, with a 4 psi change threshold as a trigger for detecting an animal being situated on a top surface of the bladder 600. Accordingly, a control unit of a treatment pad or bed may automatically or manually control the application of PEMF treatment energy according to a detection mechanism detecting the presence of an animal or subject adjacent the array. FIGS. 6B-6E show a wire loop array 500 being incorporated on top of a bladder 600 to form a treatment bed 620. However, in accordance with exemplary embodiments of the invention, the wire loop array 500 may be incorporated underneath bladder 600, between plural bladder compartments, or used in conjunction with pads or a mattress. FIG. 6B is a plan view showing the dimensions of a treatment pad or bed 620 incorporating bladder 600 according to an exemplary embodiment of the invention. As shown in FIG. 6B, a treatment pad or bed 620 incorporating a 3-by-2 array, such as array 500, may be approximately 21 inches by 33 inches for accommodating a small subject or a subject's treatment area within the 21 inch by 33 inch perimeter. As further illustrated in FIG. 6B, an end of a drive circuit 110 may be approximately 1.65 inches from an outer edge along a length of treatment bed 620 and a side of an end drive circuit 110 may be approximately 8.9 inches from an outer edge along a width of treatment bed 620. Larger pads or beds corresponding to those in 200 and 305 shown in FIGS. 2A and 3B, respectively, may be similarly constructed employing larger arrays of the inventive wire loop coil 405.

According to an exemplary embodiment of the invention, each of the generator circuits 110 of the respective treatment coils 405 may be coupled, through wired or wireless connection, to one or more controllers for programmed activation, timing control, treatment cycle interruption and reactivation, etc. According to an exemplary embodiment of the invention, each of the generator circuits 110 may also be coupled to one or more indicators, such as a LED (light-emitting diode) light, for indicating activation and deactivation of each generator circuit 110 and, correspondingly, the respective treatment coils 405.

According to an exemplary embodiment of the invention, treatment for a subject may be programmed to a 15 minute treatment session, with treatment interrupted if the RFID device (1600) detects that the subject (1610) has left the surface of the pad or bed and restarted when the subject (1610) is detected to have returned to the surface of the pad or bed. According to an exemplary embodiment, the inventive wire loops 405 with rounded indentations 410 provides for a substantially uniform field of PEMF signal amplitudes in treating a subject placed atop the treatment pad or bed 620.

According to an exemplary embodiment of the invention, the controller 1500 may be coupled, through wired or wireless connection (e.g., USB, Bluetooth, and the like), to one or more networked devices, such as a computer, a mobile telephone, and the like, for programmed features of the treatment pad/bed. The controller 1500 may also be coupled to a network interface for local or wide area network connectivity.

A pre-programmed periodic treatment regimen—for example, 15 minutes of treatment every 2, 4, 6, or 12 hours daily—for one or more RFID devices 1600 and corresponding subjects 1610 may be implemented through programmed control of the controller 1500 and generator circuits in drive units 110—for example, through user interface 1520 or via a user interface in an application program on one or more networked devices coupled to controller 1500. The controller 1500 may log treatments administered to each identified subject 1610, whereby the treatment logs may be transmitted to the one or more networked devices. According to an exemplary embodiment of the invention, the one or more networked devices—or controller 1500—may execute one or more API's (Application programming interface)—for example, for Fitbark, Heyrex, Vetrax, Open Platform, etc.—to provide for control and capture of treatments associated with individual subjects 1610 through local or wide area network connections. The application program may comprise program modules including routines, instruction sets, object components, data structures, and the like, and may be embodied as computer readable program code stored on a non-transitory computer readable medium. The non-transitory computer readable medium is any data storage device that can store data. Examples of non-transitory computer readable media include for example read-only memory, random-access memory, CD-ROMs, magnetic tape, USB keys, flash drives and optical data storage devices. The computer readable program code can also be distributed over a network including coupled computer systems so that the computer readable program code is stored and executed in a distributed fashion.

The following example is illustrative of various features and advantages of the present invention.

Example 1

Figure 7A:
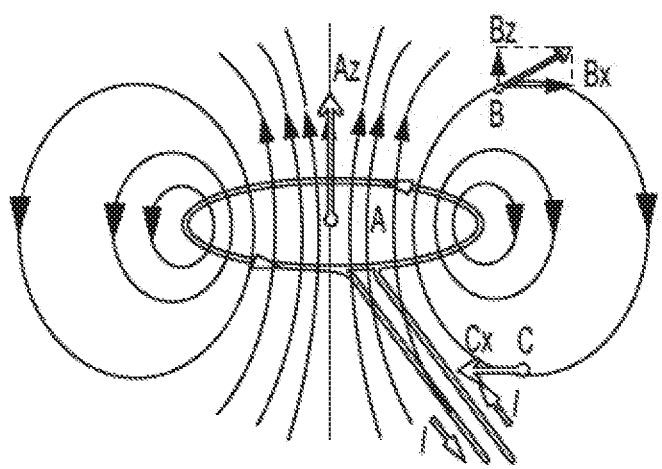
FIG. 7A is a diagram illustrating an electromagnetic field generated by an electrical current through a circular wire loop.

FIG. 7A provides an illustration of a magnetic field on a single turn coil of wire carrying current. All the magnetic field lines have closed loops around the wire coil. Thus, one of ordinary skill in the art would understand that the magnetic field forms a three dimensional torroid. For simplicity of description, explanation on the field corresponding to a treatment signal will focus on the X, Z plane through the center of the coil.

Point "A" in FIG. 7A illustrates a point at which the magnetic field may be measured during calibration of a treatment device to thereby determine a baseline magnetic field of a wire loop in correspondence with effective magnetic fields at treatment planes of respective distances from a plane of a coil array. As reflected in FIG. 7A, a majority of the magnitude at point "A" is along the Z-axis "Az". If a magnetic field probe were moved to Point "C" without rotating the probe off the Z-axis, it would not measure any significant magnetic field. To measure the magnetic field, the probe would need to be rotated to measure "Cx" along the X-axis. Point "B" has components that can be measured on both the X, and Z-axis. The resultant of "Bx" and "Bz" is the magnitude of "B" or:

$$B=\sqrt{Bx^2+Bz^2} \qquad (1)$$

To determine the magnetic field at each position the magnetic field may be measured along each axis. A three-dimensional resultant magnitude may be calculated using the equation (2):

$$B=\sqrt{Bx^2+By^2+Bz^2} \qquad (2)$$

Figure 7C:
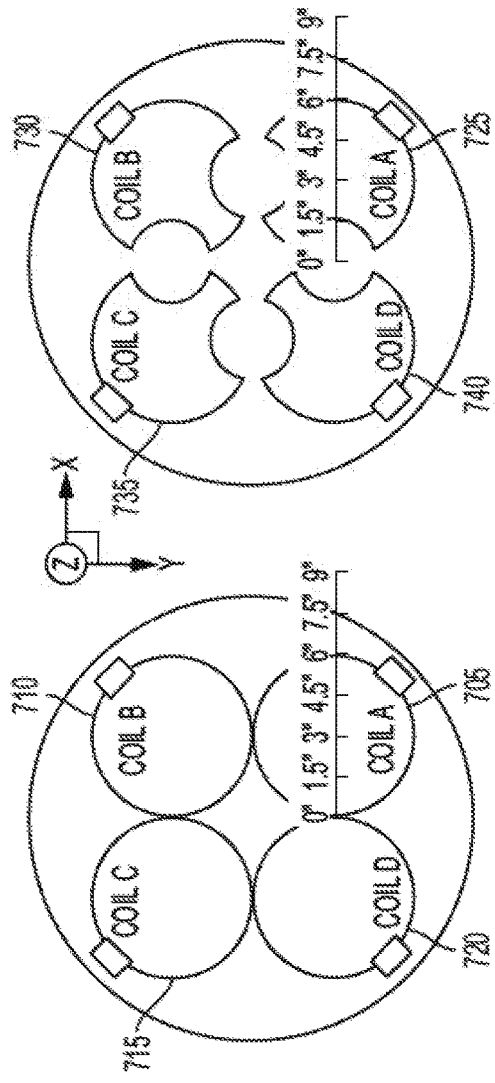

FIGS. 7B and 7C are plan views of treatment pads/beds having circular wire loops and indented wire loops (having aligned rounded indentations), respectively, conforming to the coil arrangement shown in FIG. 4C, with measurement points at 0", 1.5", 3", 4.5", 6", 7.5", and 9". As shown in FIGS. 7B and 7C, the wire loops (coils) were sized to approximately 6" in diameter and, as shown in FIG. 7C, the rounded indentations of the indented coils were aligned so as to form approximate discontinuous circles having about 1.5" radii.

The magnetic field strength was measured, along X-, Y-, and Z-axes as described above, at periodic intervals along a line—i.e., at the measurement points shown in FIGS. 7B and 7C—at a 0.5" height from a plane of coils in the treatment pads/beds. The measured field strengths were compared between a 2×2 coil bed containing circular coils (FIG. 7B) and coils with aligned rounded indentations (FIG. 7C). The measurements were made using a Tektronix® TDS2012B (ADM ID:E011) oscilloscope with a Beehive™ 100A (ADM ID: 68) H-Field Probe and a Pasternack® PE6008-50 (ADM ID: 19) 50 ohm Feed-Thru Terminator.

During calibration, the magnetic field was measured at the center of each coil with the probe oriented to be in the same plane as the coil (X,Y Plane of FIGS. 7B and 7C). At these points, the field is the most uniform and oriented along the Z-axis. All of the coils were tuned to be within 20 mVp-p of each other, as reflected in Tables 1A and 1B below.

TABLE 1A

| Coil | mVp-p |
|---|---|
| 705 | 178 |
| 710 | 176 |
| 715 | 170 |
| 720 | 170 |

TABLE 1B

| Coil | mVp-p |
|---|---|
| 725 | 174 |
| 730 | 176 |
| 735 | 180 |
| 740 | 178 |

Results of the measurements at 0.5″ from a plane of the treatment pad/bed having circular coils, as shown in FIG. 7B, are reflected in Table 2 below.

TABLE 2

| Distance (Inch) | X (mVp-p) | Y (mVp-p) | X (mVp-p) | Resultant (mVp-p) |
|---|---|---|---|---|
| 0 | 368 | 40.4 | 196 | 418.9 |
| 1.5 | 54.4 | 14.8 | 220 | 227.1 |
| 3 | 2 | 8.2 | 186 | 186.2 |
| 4.5 | 24.2 | 12.2 | 212 | 213.7 |
| 6 | 322 | 32.4 | 128 | 348.0 |
| 7.5 | 35 | 9.2 | 42.4 | 55.7 |
| 9 | 4.24 | 4.72 | 9.44 | 11.4 |

Correspondingly, results of the measurements at 0.5″ from a plane of the treatment pad/bed having coils with aligned rounded indentations, as shown in FIG. 7C, are reflected in Table 3 below.

TABLE 3

| Distance (Inch) | X (mVp-p) | Y (mVp-p) | X (mVp-p) | Resultant (mVp-p) |
|---|---|---|---|---|
| 0 | 60 | 12 | 86 | 105.5 |
| 1.5 | 166 | 27.6 | 162 | 233.6 |
| 3 | 4.4 | 6.32 | 164 | 164.2 |
| 4.5 | 23.4 | 2 | 176 | 177.6 |
| 6 | 218 | 8.32 | 150 | 264.8 |
| 7.5 | 30 | 2 | 35.2 | 46.3 |
| 9 | 3 | 2 | 12.4 | 12.9 |

Due to the symmetrical geometry of the coil configurations, the magnetic field along the line formed by the measurement points at coils 705 and 725, as shown in FIGS. 7B and 7C, is a mirror image of magnetic field along the same line extending through coils 720 and 740.

Figure 7E:
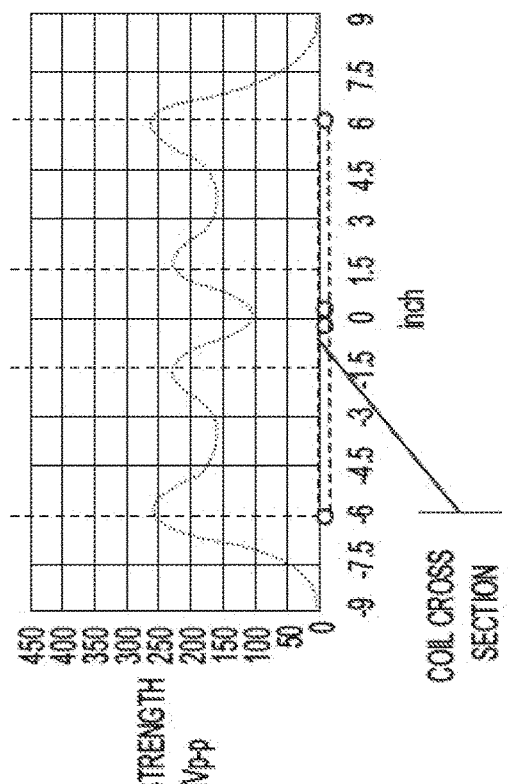
FIGS. 7D and 7E are graphs showing near field measurement results for Example 1 corresponding to measurement points shown in FIGS. 7B and 7C.
Figure 7D:
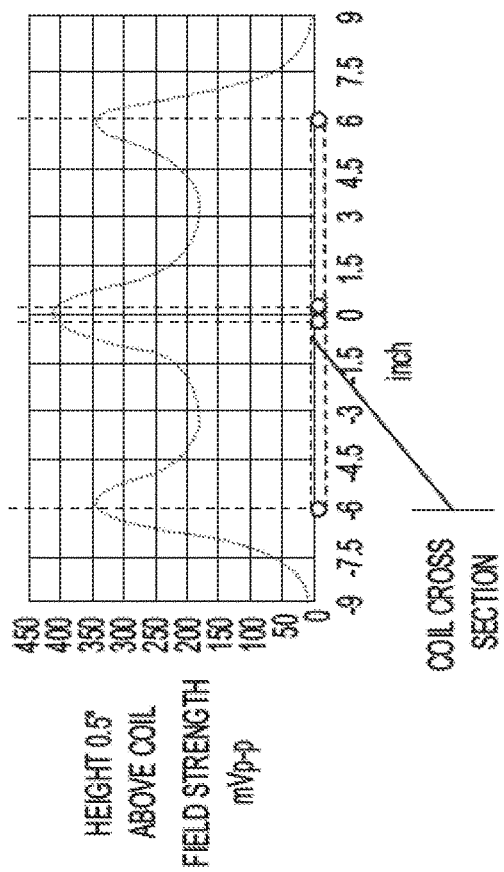

FIGS. 7D and 7E are graphs showing near field measurement results for Example 1 corresponding to measurement points shown in FIGS. 7B and 7C and the mirror image of the results extending through coils 720 and 740 shown in FIGS. 7B and 7C. The bottoms of FIGS. 7D and 7E incorporate graphic representations of the corresponding coil cross sections, with vertical dashed lines showing that the near field peaks are directly over the coil wires.

As shown in Table 3 and FIG. 7E, the resultant measured magnetic field output at 0.5″ height from the indented coil array had a standard deviation of 62.15 between measurement points at 0″ and 6″, whereas the measured output for the circular coil array had a standard deviation of 99.88 for the corresponding measurement points, as shown in Table 2 and FIG. 7D. Correspondingly, the range of measured outputs for the indented coil array was 105.5 to 264.8 mVp-p (or 159.3 mVp-p) between measurement points 0″ and 6″ and the range of measured outputs for the circular coil array was 186.2 to 418.9 mVp-p (or 232.7 mVp-p) between measurement points 0″ and 6″. Thus, the measurements showed that in the near field (0.5 inch above the plane of the coil) the treatment pad/bed having coils with aligned rounded indentations had a more consistent level and the treatment pad/bed having circular coils showed more varied output depending on coil wire position.

Measurements were also made at a higher plane, i.e. 3-5 inches from the plane of the array, and the signal profile became more uniform such that effective treatment may be provided by both a circular wire loop array and an indented wire loop array.

While in the foregoing specification a detailed description of specific embodiments of the invention was set forth, it will be understood that many of the details herein given may be varied considerably by those skilled in the art without departing from the spirit and scope of the invention.

The invention claimed is:

1. An apparatus for providing pulsed electromagnetic field (PEMF) treatment, comprising:
   an enclosure;
   a plurality of electrically-conductive loops arranged within the enclosure to form an array, each of the plurality of electrically-conductive loops having a generally circular circumference with one or more indentations aligned with a corresponding indentation of an adjacent one of the plurality of electrically-conductive loops; and
   a controlling device coupled to the plurality of electrically-conductive loops, the controlling device configured to control a generation of one or more PEMF signals at the plurality of electrically-conductive loops.

2. The apparatus of claim 1, wherein each pair of the aligned indentations in adjacent electrically-conductive loops form a discontinuous substantially circular shape.

3. The apparatus of claim 2, wherein a diameter of the discontinuous substantially circular shape is between approximately 2 inches and 6 inches.

4. The apparatus of claim 1, wherein each electrically-conductive loopy has a diameter of between approximately 5 inches and 8 inches.

5. The apparatus of claim 1, wherein the controlling device communicates with one or more wireless devices over a network connection.

6. The apparatus of claim 5, wherein
   the one or more wireless devices are adapted to detect the one or more PEMF signals, and
   upon a condition of at least one of the one or more wireless devices detecting the one or more PEMF signals, the controlling device controls, based on one or more communications from the at least one of the one or more wireless devices, the generation of another one or more PEMF signals that are associated with the at least one of the one or more wireless devices at the plurality of electrically-conductive loops.

7. The apparatus of claim 5, wherein the one or more wireless devices each comprise a radio frequency identification (RFID) device.

8. An apparatus for treating a subject by applying one or more pulsed electromagnetic field (PEMF) signals, comprising:
one or more generator circuits each configured to generate a radio frequency (RF) signal;
an array of plural loop antennas each coupled to one of the one or more generator circuits, each of the plurality loop antennas comprising a conductor coil having a generally circular shape with one or more rounded indentations in said generally circular shape; and
an enclosure configured to house at least the array of plural loop antennas, said enclosure comprising a treatment surface configured to be disposed proximate the subject, wherein each of the plurality of rounded indentations of each loop antenna is aligned with one of the plurality of rounded indentations of an adjacent loop antenna in the array.

9. The apparatus of claim 8, wherein each pair of the aligned rounded indentations in adjacent loop antennas form a discontinuous substantially circular shape.

10. The apparatus of claim 9, wherein a diameter of the discontinuous substantially circular shape formed between adjacent wire loops is between approximately 2 inches and 6 inches.

11. The apparatus of claim 8, wherein the conductor coil of the each of the plural loop antennas has a diameter of between approximately 5 inches and 8 inches.

12. The apparatus of claim 8, further comprising one or more control circuits coupled to the one or more generator circuits, said one or more control circuits being configured to control activation of each of the plurality of generator circuits.

13. The apparatus of claim 12, wherein the one or more control circuits are coupled to, via one or more of a wired connection and a wireless connection, a computing apparatus, said computing apparatus configured to execute one or more programs adapted to generate instructions for the one or more control circuits.

14. The apparatus of claim 13, wherein the computing apparatus communicates with one or more wireless devices over a network connection.

15. The apparatus of claim 14, wherein
the one or more wireless devices are adapted to detect the one or more RF signals from the one or more generator circuits via the array of plural loop antennas, and
upon a condition of at least one of the one or more wireless devices detecting the one or more RF signals, the computing apparatus controls, based on one or more communications from the at least one wireless device, the one or more generator circuits to generate another one or more RF signals that are associated with the at least one wireless device via the array of plural loop antennas.

16. The apparatus of claim 14, wherein the one or more wireless devices each comprise a radio frequency identification (RFID) device.

17. A method for treating a subject by applying one or more pulsed electromagnetic field (PEMF) signals, comprising:
providing an array of a plurality of loop antennas coupled to a corresponding one or more generator circuits in an enclosure configured to house at least the array of plural loop antennas, said enclosure comprising a treatment surface configured to be placed proximate the subject;
activating one or more of the generator circuits to generate one or more preliminary treatment signals to corresponding one or more of the loop antennas;
detecting a presence of the subject;
upon a condition of detecting the subject being proximate the treatment surface, activating the one or more of the generator circuits to generate another one or more treatment signals associated with the subject to the corresponding one or more loop antennas,
wherein each loop antenna comprises a conductor coil have a generally circular shape with a plurality of rounded indentations in said generally circular shape.

18. The method of claim 17, wherein the one or more treatment signals are generated in accordance with a pre-programmed schedule.

19. The method of claim 17, wherein the detecting is conducted by one or more wireless devices that are in communication with one or more computing apparatuses coupled to the one or more generator circuits, the one or more wireless devices detecting the one or more preliminary treatment signals.

20. A system for providing pulsed electromagnetic field (PEMF) treatment, comprising:
one or more wireless devices; and
a PEMF treatment apparatus, the PEMF treatment apparatus comprising:
an enclosure;
a plurality of electrically-conductive loops arranged within the enclosure to form an array, each of the plurality of electrically-conductive loops having a generally circular circumference with one or more indentations aligned with a corresponding indentation of an adjacent one of the plurality of electrically-conductive loops; and
a controlling device coupled to the plurality of electrically-conductive loops, the controlling device configured to control a generation of one or more PEMF signals at the plurality of electrically-conductive loops,
wherein the one or more wireless devices are adapted to detect the one or more PEMF signals, and
upon the condition of at least one of the one or more wireless devices detecting the one or more PEMF signals, the controlling device controls the generation of another one or more PEMF signals that are associated with the at least one wireless device at the plurality of electrically-conductive loops.

21. The system of claim 20, wherein the one or more wireless devices each comprise a radio frequency identification (RFID) device.

* * * * *